(12) United States Patent
Clausen et al.

(10) Patent No.: US 10,919,973 B2
(45) Date of Patent: *Feb. 16, 2021

(54) GENERATION OF A CANCER-SPECIFIC IMMUNE RESPONSE TOWARD MUC1 AND CANCER SPECIFIC MUC1 ANTIBODIES

(71) Applicants: Københavns Universitet, Copenhagen N (DK); Cancer Research Technology Limited, London (GB)

(72) Inventors: Henrik Clausen, Holte (DK); Joy Burchell, London (GB); Ulla Mandel, Holte (DK); Anne Louise Sørensen, Copenhagen S (DK); Mads Agervig Tarp, Kgs. Lyngby (DK); Joyce Taylor-Papadimitriou, London (GB)

(73) Assignees: KOBENHAVNS UNIVERRSITET, Copenhagen (DK); CANCER RESEARCH TECHNOLOGY LIMITED, London (GB)

( * ) Notice: Subject to any disclaimer, the term of this patent is extended or adjusted under 35 U.S.C. 154(b) by 35 days.

This patent is subject to a terminal disclaimer.

(21) Appl. No.: 16/006,119

(22) Filed: Jun. 12, 2018

(65) Prior Publication Data

US 2018/0334507 A1 Nov. 22, 2018

Related U.S. Application Data

(63) Continuation of application No. 15/040,375, filed on Feb. 10, 2016, now Pat. No. 10,017,576, which is a (Continued)

(51) Int. Cl.
*C40B 30/06* (2006.01)
*C07K 16/28* (2006.01)
(Continued)

(52) U.S. Cl.
CPC ...... *C07K 16/2896* (2013.01); *A61K 39/0011* (2013.01); *A61K 39/00117* (2018.08);
(Continued)

(58) Field of Classification Search
None
See application file for complete search history.

(56) References Cited

U.S. PATENT DOCUMENTS

| 5,876,716 A | 3/1999 | Hansen et al. |
| 6,465,220 B1 | 10/2002 | Hassan et al. |

(Continued)

FOREIGN PATENT DOCUMENTS

| WO | WO 99/34824 A2 | 7/1999 |
| WO | WO 01/85215 A2 | 11/2001 |

(Continued)

OTHER PUBLICATIONS

Burchell, Joy M. et al., "O-Linked Glycosylation in the Mammary Gland: Changes that Occur During Malignancy" Journal of Mammary Gland Biology and Neoplasia, 2001, pp. 355-364, vol. 6, No. 3.

(Continued)

*Primary Examiner* — Christian C Boesen
(74) *Attorney, Agent, or Firm* — Knobbe, Martens, Olson & Bear LLP

(57) ABSTRACT

The present invention provides a method for inducing a cancer specific immune response against MUC1 using an immunogenic glycopeptide. Other aspects of the invention are a pharmaceutical composition comprising the immunogenic glycopeptide and a cancer vaccine comprising the immunogenic glycopeptide. Another aspect is an antibody generated using the immunogenic glycopeptide and the use of said antibody in therapy and diagnosis.

11 Claims, 17 Drawing Sheets

Figure 1:
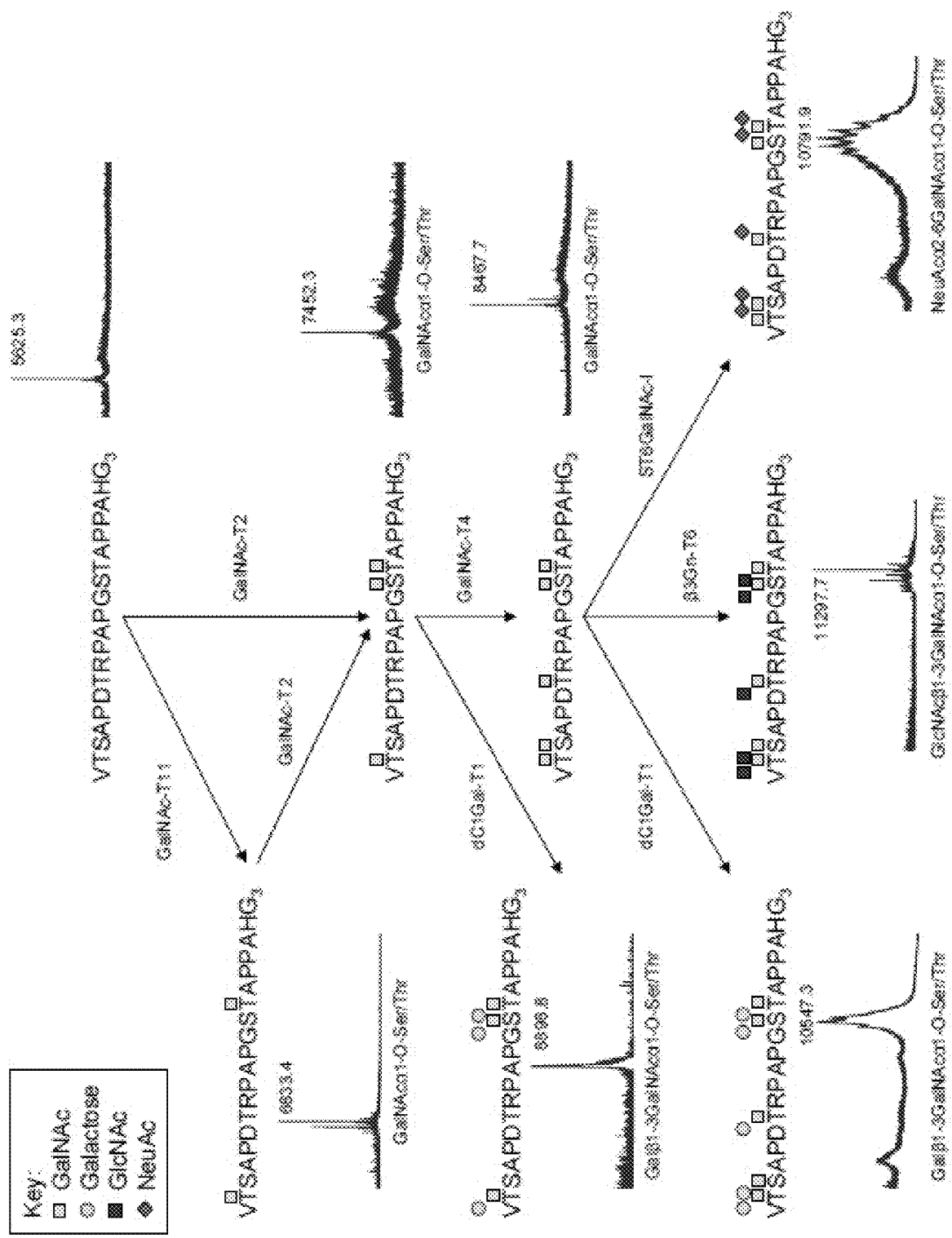

Specification includes a Sequence Listing.

Related U.S. Application Data continuation of application No. 14/539,916, filed on Nov. 12, 2014, now Pat. No. 9,359,436, which is a continuation of application No. 13/864,096, filed on Apr. 16, 2013, now Pat. No. 8,912,311, which is a continuation of application No. 12/444,360, filed as application No. PCT/DK2007/050139 on Oct. 4, 2007, now Pat. No. 8,440,798.

(60) Provisional application No. 60/848,997, filed on Oct. 4, 2006.

(51) Int. Cl.

| | |
|---|---|
| A61K 47/64 | (2017.01) |
| A61K 39/00 | (2006.01) |
| C07K 14/47 | (2006.01) |
| C07K 16/30 | (2006.01) |
| G01N 33/574 | (2006.01) |
| G01N 33/68 | (2006.01) |
| C40B 30/04 | (2006.01) |
| C40B 50/06 | (2006.01) |

(52) U.S. Cl.
CPC ........ *A61K 47/646* (2017.08); *C07K 14/4727* (2013.01); *C07K 16/28* (2013.01); *C07K 16/30* (2013.01); *C07K 16/3092* (2013.01); *G01N 33/574* (2013.01); *G01N 33/6854* (2013.01); *A61K 2039/5154* (2013.01); *A61K 2039/5158* (2013.01); *A61K 2039/6031* (2013.01); *A61K 2039/6037* (2013.01); *A61K 2039/6075* (2013.01); *A61K 2039/6081* (2013.01); *C07K 2317/14* (2013.01); *C07K 2317/34* (2013.01); *C07K 2317/76* (2013.01); *C40B 30/04* (2013.01); *C40B 30/06* (2013.01); *C40B 50/06* (2013.01); *Y02A 50/30* (2018.01)

(56) References Cited

U.S. PATENT DOCUMENTS

| | | |
|---|---|---|
| 7,282,567 B2 | 10/2007 | Goldenberg et al. |
| 8,440,798 B2 | 5/2013 | Clausen et al. |

FOREIGN PATENT DOCUMENTS

| | | |
|---|---|---|
| WO | WO 03/089574 A2 | 10/2003 |
| WO | WO 2004/022590 A2 | 3/2004 |
| WO | WO 2004/042075 A2 | 5/2004 |

OTHER PUBLICATIONS

Clausen, Henrik et al., "Monoclonal Antibodies Directed to the Blood Group A Associated Structure, Galactosyl-A: Specificity and Relation to the Thomsen-Friedenreich Antigen" Molecular Immunology, 1988, pp. 199-204, vol. 25, No. 2.

Decision of Rejection for JP 2009-530756 dated Sep. 17, 2013.
Engelmann, Katja et al., "Identification and Topology of Variant Sequences within Individual Repeat Domains of the Human Epithelial Tumor Mucin MUC1" The Journal of Biological Chemistry, 2001, pp. 27764-27769, vol. 276, No. 30.
Hanisch, Franz-Georg et al., "Monoclonal Antibody BW835 Defines a Site-specific Thomsen-Friedenreich Disaccharide Linked to Threonine within the VTSA Motif of MUC1 Tandem Repeats" Cancer Research, Sep. 15, 1995, pp. 4036-4040, vol. 55.
Hirohashi, Setsuo et al., "Blood group A cross-reacting epitope defined by monoclonal antibodies NCC-LU-35 and -81 expressed in cancer of blood group O or B individuals: Its identification as Tn antigen" Proc. Natl. Acad. Sci. USA, Oct. 1985, pp. 7039-7043, vol. 82.
Kjeldsen T. et al., "Coexpression of Sialosyl-Tn (Neuac-Alpha-2-]6Galnac-Alpha-1-]O-Ser/Thr) and Tn (Galnac-Alpha-1-]O-Ser/Thr) Blood-Group Antigens on Tn Erythrocytes" Vox Sanguinis, 1989, pp. 81-87, vol. 57.
Kjeldsen, Thomas et al., "Preparation and Characterization of Monoclonal Antibodies Directed to the Tumor-associated 0-linked Sialosyl1-2→6 α-N-Acetylgalactosaminyl (Sialosyl-Tn) Epitope" Cancer Research, Apr. 15, 1988, pp. 2214-2220, vol. 48.
Marcos, Nuno T. et al., "Polypeptide GalNAc-transferases, ST6GalNAc-transferase I, and ST3Gal-transferase I Expression in Gastric Carcinoma Cell Lines" The Journal of Histochemistry & Cytochemistry, 2003, pp. 761-771, vol. 51, No. 6.
Mensdorff-Pouilly, Sivia Von et al., "Reactivity of Natural and Induced Human Antibodies to MUC1 Mucin with MUC1 Peptides and N-Acetylgalactosamine (GaINAc) Peptides" Int. J. Cancer, 2000, pp. 702-712, vol. 86.
Reis, Celso A. et al., "Characterization of a Panel of Monoclonal Antibodies Using GalNAc Glycosylated Peptides and Recombinant MUC1" Tumor Biology, Dec. 1997, pp. 127-133, vol. 19, Suppl. 1.
Reis, Celso A. et al., "Development and characterization of an antibody directed to an a-N-acetyl-D-galactosamine glycosylated MUC2 peptide" Glycoconjugate Journal, 1998, pp. 51-62, vol. 15.
Rose, Mary Callaghan, et al. "Effects of Deglycosylationon the Architecture of Ovine Submaxillary Mucin Glycoprotein", *The Journal of Biological Chemistry* 259(5):3167-3172, Mar. 10, 1984.
Sorensen, Anne Louise et al., "Chemoenzymatically synthesized multimeric Tn/STn MUC1 glycopeptides elicit cancer-specific anti-MUC1 antibody responses and override tolerance" Glycobiology, 2006, pp. 96-107, vol. 16, No. 2.
Springer, Georg F. "T and Tn, general Carcinoma Autoantigens" Science, New Series, Jun. 15, 1984, pp. 1198-1206, vol. 224, No. 4654.
Takeuchi, Hideyuki et al., "The epitope recognized by the unique anti-MUC1 monoclonal antibody MY.1E12 involves sialylα2-3galactosylβ1-3N-acetylgalactosaminide linked to a distinct threonine residue in the MUC1 tandem repeat" Journal of Immunological Methods, 2002, pp. 199-209, vol. 270.
Thurnher et al., "Use of O-glycosylation-defective human lymphoid cell lines and flow cytometry to delineate the specificity of Moluccella laevis lectin and monoclonal antibody 5F4 for the Tn antigen, (GaINAc alpha 1-O-Ser/Thr)," Immunol. Lett. Jun. 1993; 36(3): 239-43.
Yamamoto, Masay et al., "A Novel Monoclonal Antibody Specific for Sialylated MUC1 Mucin" Jpn. J. Cancer Res., May 1996, pp. 488-496, vol. 87.

Biotinylated MUC1 60-mer

|        | V | T | S | A | P | D | T | R | P | A | P | G | S | T | A | P | P | A | H | G | (n=3) |
|--------|---|---|---|---|---|---|---|---|---|---|---|---|---|---|---|---|---|---|---|---|-------|
| 6Tn    |   |   |   |   |   |   |   |   |   |   |   |   |   |   |   | □ | □ |   |   |   |       |
| 9Tn    |   |   |   |   |   |   |   |   |   |   |   |   |   | □ |   | □ | □ |   |   |   |       |
| 15Tn   | □ | □ |   |   |   |   |   | □ |   |   |   |   |   | □ |   | □ | □ |   |   |   |       |
| 9STn   |   |   |   |   |   |   |   |   |   |   |   |   |   | ◆ |   | ◆ | ◆ |   |   |   |       |
| 15STn  | ◆ | ◆ |   |   |   |   |   | ◆ |   |   |   |   |   | ◆ |   | ◆ | ◆ |   |   |   |       |
| 9T     |   |   |   |   |   |   |   |   |   |   |   |   |   | ● |   | ● | ● |   |   |   |       |
| 15T    | ● | ● |   |   |   |   |   | ● |   |   |   |   |   | ● |   | ● | ● |   |   |   |       |
| 9ST    |   |   |   |   |   |   |   |   |   |   |   |   |   | × |   | × | × |   |   |   |       |
| 15ST   | × | × |   |   |   |   |   | × |   |   |   |   |   | × |   | × | × |   |   |   |       |
| 9Core3 |   |   |   |   |   |   |   |   |   |   |   |   |   | ▲ |   | ▲ | ▲ |   |   |   |       |
| 15Core3| ▲ | ▲ |   |   |   |   |   | ▲ |   |   |   |   |   | ▲ |   | ▲ | ▲ |   |   |   |       |

Biotinylated MUC1 25-mer valine-substituted

|            | T | A | P | P | A | H | G | V | T | S | A | P | D | T | R | P | A | P | G | S | T | A | P | P | A |
|------------|---|---|---|---|---|---|---|---|---|---|---|---|---|---|---|---|---|---|---|---|---|---|---|---|---|
| TAP25V9    |   |   |   |   |   |   |   | V |   |   |   |   |   |   |   |   |   |   |   |   |   |   |   |   |   |
| 2Tn-TAP25V9| □ |   |   |   |   |   |   | V |   |   |   |   |   |   |   |   |   |   |   |   |   |   |   |   |   |
| TAP25V21   |   |   |   |   |   |   |   |   |   |   |   |   |   |   |   |   |   |   |   |   |   |   |   | V |   |
| 2Tn-TAP25V21| □ |   |   |   |   |   |   |   |   |   |   |   |   |   |   |   |   |   |   |   |   |   |   | V |   |

MUC1 21-mer

|       | A | H | G | V | T | S | A | P | D | T | R | P | A | P | G | S | T | A | P | P | A |
|-------|---|---|---|---|---|---|---|---|---|---|---|---|---|---|---|---|---|---|---|---|---|
| Tn-A1 |   |   |   |   | □ |   |   |   |   |   |   |   |   |   |   |   |   |   |   |   |   |
| Tn-A2 |   |   |   |   |   |   |   |   |   |   |   |   |   |   |   |   |   |   |   |   |   |
| Tn-A3 |   |   |   |   |   |   |   |   |   |   |   |   |   |   |   |   |   |   |   |   | □ |
| Tn-A4 |   |   |   |   |   |   |   |   |   |   |   |   |   |   |   |   |   |   |   |   |   |
| T-A1  |   |   |   |   | ● |   |   |   |   |   |   |   |   |   |   |   |   |   |   |   |   |
| T-A2  |   |   |   |   |   |   |   |   |   |   |   |   |   |   |   |   |   |   |   |   |   |
| T-A3  |   |   |   |   |   |   |   |   |   |   |   |   |   |   |   |   |   |   |   |   | ● |
| T-A4  |   |   |   |   |   |   |   |   |   |   |   | ● |   |   |   |   |   |   |   |   |   |

Key to glycans: □: Tn; ◆: STn; ●: T; ×: ST; ▲: Core 3.

*FIG. 5*

2D9

5E10

SM3

SEQUENCE LISTING

```
<160> NUMBER OF SEQ ID NOS: 14

<210> SEQ ID NO 1
<211> LENGTH: 20
<212> TYPE: PRT
<213> ORGANISM: Homo sapiens

<400> SEQUENCE: 1

Val Thr Ser Ala Pro Asp Thr Arg Pro Ala Pro Gly Ser Thr Ala Pro
1               5                   10                  15

Pro Ala His Gly
            20

<210> SEQ ID NO 2
<211> LENGTH: 4
<212> TYPE: PRT
<213> ORGANISM: Homo sapiens

<400> SEQUENCE: 2

Gly Ser Thr Ala
1

<210> SEQ ID NO 3
<211> LENGTH: 5
<212> TYPE: PRT
<213> ORGANISM: Homo sapiens

<400> SEQUENCE: 3

Gly Ser Thr Ala Pro
1               5

<210> SEQ ID NO 4
<211> LENGTH: 4
<212> TYPE: PRT
<213> ORGANISM: Homo sapiens

<400> SEQUENCE: 4

Pro Asp Thr Arg
1

<210> SEQ ID NO 5
```

```
<211> LENGTH: 7
<212> TYPE: PRT
<213> ORGANISM: Homo sapiens

<400> SEQUENCE: 5

Thr Arg Pro Ala Pro Gly Ser
1               5

<210> SEQ ID NO 6
<211> LENGTH: 4
<212> TYPE: PRT
<213> ORGANISM: Homo sapiens

<400> SEQUENCE: 6

Val Thr Ser Ala
1

<210> SEQ ID NO 7
<211> LENGTH: 4
<212> TYPE: PRT
<213> ORGANISM: Homo sapiens

<400> SEQUENCE: 7

Gly Ser Thr Ala
1

<210> SEQ ID NO 8
<211> LENGTH: 20
<212> TYPE: PRT
<213> ORGANISM: Homo sapiens

<400> SEQUENCE: 8

Pro Thr Thr Thr Pro Ile Ser Thr Thr Met Val Thr Pro Thr Pro
1               5                   10                  15

Thr Pro Thr Cys
            20

<210> SEQ ID NO 9
<211> LENGTH: 21
<212> TYPE: PRT
<213> ORGANISM: Homo sapiens

<400> SEQUENCE: 9

Cys Pro Leu Pro Val Thr Asp Thr Ser Ser Ala Ser Thr Gly His Ala
1               5                   10                  15

Thr Pro Leu Pro Val
            20

<210> SEQ ID NO 10
<211> LENGTH: 25
<212> TYPE: PRT
<213> ORGANISM: Homo sapiens

<400> SEQUENCE: 10

Thr Ala Pro Pro Ala His Gly Val Val Ser Ala Pro Asp Thr Arg Pro
1               5                   10                  15

Ala Pro Gly Ser Thr Ala Pro Pro Ala
            20                  25

<210> SEQ ID NO 11
<211> LENGTH: 25
<212> TYPE: PRT
<213> ORGANISM: Homo sapiens
```

```
<400> SEQUENCE: 11

Thr Ala Pro Pro Ala His Gly Val Thr Ser Ala Pro Asp Thr Arg Pro
1               5                   10                  15

Ala Pro Gly Ser Val Ala Pro Pro Ala
            20              25

<210> SEQ ID NO 12
<211> LENGTH: 21
<212> TYPE: PRT
<213> ORGANISM: Homo sapiens

<400> SEQUENCE: 12

Ala His Gly Val Thr Ser Ala Pro Asp Thr Arg Pro Ala Pro Gly Ser
1               5                   10                  15

Thr Ala Pro Pro Ala
            20

<210> SEQ ID NO 13
<211> LENGTH: 4
<212> TYPE: PRT
<213> ORGANISM: Homo sapiens

<400> SEQUENCE: 13

Gly Ser Thr Val
1

<210> SEQ ID NO 14
<211> LENGTH: 33
<212> TYPE: PRT
<213> ORGANISM: Homo Sapiens

<400> SEQUENCE: 14

Pro Thr Thr Thr Pro Ile Thr Thr Thr Thr Thr Val Thr Pro Thr Pro
1               5                   10                  15

Thr Pro Thr Gly Thr Gln Thr Pro Thr Thr Thr Pro Ile Ser Thr Thr
            20                  25                  30

Cys
```

GENERATION OF A CANCER-SPECIFIC IMMUNE RESPONSE TOWARD MUC1 AND CANCER SPECIFIC MUC1 ANTIBODIES

CROSS-REFERENCE TO RELATED APPLICATIONS

This application is a continuation of U.S. application Ser. No. 15/040,375, filed on Feb. 10, 2016, which is a continuation of U.S. application Ser. No. 14/539,916, filed on Nov. 12, 2014, which claims the benefit of U.S. application Ser. No. 13/864,096, filed on Apr. 16, 2013, which claims the benefit of U.S. application Ser. No. 12/444,360, filed on Oct. 22, 2009, which claims the benefit and priority to and is a U.S. National Phase Application of PCT International Application Number PCT/DK2007/050139, filed on Oct. 4, 2007, designating the United States of America and published in the English language, which is an International Application of and claims the benefit of priority to U.S. Provisional Application No. 60/848,997, filed on Oct. 4, 2006. The disclosures of the above-referenced applications are hereby expressly incorporated by reference in their entireties.

SEQUENCE LISTING IN ELECTRONIC FORMAT

The present application is being filed along with a Sequence Listing in electronic format. The sequence listing is provided as a file entitled "2018 Jun. 11 Sequence Listing—PLOUG79.001C4", created Jun. 11, 2018, which is 4 KB in size. The information in the electronic format of the sequence listing is incorporated herein by reference in its entirety.

BACKGROUND

The human mucin MUC1 is a polymorphic transmembrane glycoprotein expressed on the apical surfaces of simple and glandular epithelia. MUC1 is highly over-expressed and aberrantly O-glycosylated in adenocarcinomas. The extracellular domain of the mucin contains variable number of tandem repeats (25-125) of 20 amino acid residues with five potential sites for O-glycosylation. O-glycans are incompletely processed in cancer cells resulting in the expression of the pancarcinoma carbohydrate antigens Tn (GalNAcα1-O-Ser/Thr), STn (NeuAcα2-6GalNAcα1-O-Ser/Thr), and T (Galβ1-3GalNAcα1-O-Ser/Thr). MUC1 expressed by breast carcinoma cells carries the short cancer-associated Tn, STn, and T antigens as well as the mono- and disialyl core 1 structure (ST, NeuAcα2-3Galβ1-3 [NeuAcα2-6]+/−GalNAcα1-O-Ser/Thr) found widely in normal cells. In contrast, MUC1 expressed in normal breast epithelial cells generally carry branched core 2 O-glycans (Galβ1-3[GlcNAcβ1-6] GalNAcα1-O-Ser/Thr) with lactosamine extensions. The cell membrane bound mucin MUC1 has long been considered a prime target for immunotherapeutic intervention. The existence of anti-MUC1 antibodies and circulating immune complexes containing MUC1 in breast cancer patients that correlates with improved prognosis, clearly supports MUC1 as a target. However, stimulation of an effective cellular or humoral immune response to cancer-associated forms of MUC1 in patients or transgenic animals expressing the human MUC1 gene (using defined immunogens as opposed to cell based therapies) have not been achieved. Strategies for active specific immunotherapy based on peptide/protein immunogens have so far been limited to unglycosylated MUC1 tandem repeat peptides of different lengths, conjugated to different carriers, or administered with an adjuvant. These strategies have generally failed to produce effective immune responses to MUC1 expressed by cancer cells in hosts where the mucin is expressed as a self antigen.

In the past, a large number of monoclonal antibodies (MAbs) have been produced to purified MUC1 and synthetic peptides and glycopeptides derived from MUC1. The epitopes of these MAbs have traditionally been defined by scanning overlapping short peptides, and most of the MAbs define epitopes in the heavily O-glycosylated mucin tandem repeat domain. One large group of MAbs have been raised against human milk fat globule (HMFG) including HMFG1, 115D8, and SM3, most of which react with an epitope in the PDTR (SEQ ID NO. 4) region of the MUC1 tandem repeat considered to be the immunodominant peptide epitope in wild type mice. Only a few MAbs defining tandem repeat epitopes outside the PDTR (SEQ ID NO: 4) region have been reported. One generated against breast cancer tissue extract, DF3, is used in the CA 15-3 screening assay in combination with 115D8 and defines the peptide epitope TRPAPGS (SEQ ID NO. 5). Immunization with unglycosylated MUC1 peptide has given rise to a low-affinity monoclonal antibody (BCP9) reactive with the GSTAP (SEQ ID NO. 3) peptide.

Most MUC1 antibodies react with the peptide backbone but often the binding is modulated by the presence of glycans. In some cases the presence of a particular glycan can enhance binding as seen with B27.29, 115D8, and VU-2-G7. In other examples glycans can inhibit binding, as seen with SM3 and HMFG1. SM3 was raised against chemically deglycosylated HMFG and exhibits high preference for cancer-associated MUC1—opposed to other MAbs raised against HMFG—because the antibody binding to the PDTR (SEQ ID NO. 4) region is selectively blocked by large branched O-glycans as found in normal breast epithelium (Burchell et al. 2001).

A few antibodies reacting specifically with MUC1 glycoforms have been reported. One MAb, BW835, was generated by alternating injections of cancer cell lines MCF-7 and SW-613, and the specificity is reported to be restricted to the glycopeptide epitope VTSA (SEQ ID NO. 6) where Thr is substituted with the T antigen (Galβ1-3GalNAcα1-O-Ser/Thr) (Hanisch et al. 1995). The MAb MY.1E12 (Yamamoto et al. 1996) was raised against HMFG and the epitope maps to the same peptide sequence, but here sialylation of the T structure (ST) enhances reactivity (Takeuchi et al. 2002).

Recently, we found that immunization with long Tn- or STn-MUC1 tandem repeat glycopeptides can override tolerance in humanized MUC1 transgenic Balb/c mice (Sorensen et al. 2006 and example 1 of the present specification). The humoral immune response induced with the glycopeptide vaccines was highly specific for the Tn/STn-MUC1 glycoforms and MUC1 expressed by human cancer cells. In order to further characterize immunity to these glycopeptides, we generated monoclonal antibodies that mimic the polyclonal response elicited in MUC1 transgenic mice.

SUMMARY OF THE INVENTION

The present invention provides a method for inducing a highly cancer-associated or cancer specific immune response against MUC1 using an immunogenic glycopeptide. Other aspects of the invention are a pharmaceutical composition comprising the immunogenic glycopeptide and a cancer vaccine comprising the immunogenic glycopeptide. Another aspect is an antibody generated using the immunogenic glycopeptide and the use of said antibody in therapy and diagnosis.

DETAILED DESCRIPTION OF THE INVENTION

Method of Inducing a Cancer Specific Immune Response Toward MUC1.

Surprisingly, immunization with an immunogenic glycopeptide comprising a glycosylated GSTA (SEQ ID NO. 7) motif has been shown to induce a cancer specific immune response toward MUC1. E.g. it has been shown that humoral immunity toward cancer cells can be generated.

When referring to the "immunogenic glycopeptide" herein, what is meant are all the embodiments described below of the immunogenic glycopeptide used for inducing a cancer specific immune response.

Thus, one aspect of the present invention is directed to a method of inducing a cancer specific immune response toward MUC1 comprising immunization of a mammal with an immunogenic glycopeptide comprising a GSTA (SEQ ID NO. 7) motif, wherein said GSTA (SEQ ID NO. 7) motif is O-glycosylated at least at the T-residue or at the S-residue of the GSTA (SEQ ID NO. 7) motif.

Preferably, the mammal is selected from the group consisting of: a human, a mouse, a rat, a rabbit, a sheep, a goat, and a dog.

In a preferred embodiment, the immune response toward MUC1 is either innate immunity, humoral immunity, cellular immunity or any combinations hereof.

In another preferred embodiment, MUC1 is aberrantly glycosylated and expressed on cancer cells. I.e. the immune response is preferentially directed toward MUC1 that is aberrantly glycosylated and expressed on cancer cells and to a lesser degree toward MUC1 with a normal glycosylation pattern, e.g. branched core 2-based structures.

As referred to herein, a GSTA (SEQ ID NO. 7) motif is a stretch of four amino acids, wherein the letters denote the identity of the amino acids with the one-letter amino acid code.

An O-glycosylation as referred to herein denotes the presence of a sugar group at the hydroxyl group of the side chain of serine or threonine.

A Tn glycosylation as referred to herein can also be described as (GalNAcα1-O-Ser/Thr), i.e. GalNAcα1 substitution at the side chain hydroxyl of a serine or a threonine.

An STn glycosylation as referred to herein can also be described as (NeuAcα2-6GalNAcα1-O-Ser/Thr), i.e. NeuAcα2-6GalNAcα1 substitution at the side chain hydroxyl of a serine or a threonine. The sialic acid of STn may be O-acetylated at any —OH position.

Preferably, the O-glycosylation of the GSTA (SEQ ID NO. 7) motif is either an STn glycan or a Tn glycan.

In a preferred embodiment, the S-residue and T-residue of the GSTA (SEQ ID NO. 7) motif is O-glycosylated at the same time. In this embodiment, the S and T residue may carry the same O-glycosylation or they may carry different O-glycosylations.

Thus, in a preferred embodiment, the O-glycosylation of the S-residue and the T-residue is either STn glycan or Tn glycan.

In another preferred embodiment, the GSTA (SEQ ID NO. 7) motif is present in a tandem repeat of 20 amino acid residues, said tandem repeat comprising five potential sites for O-glycosylation.

As referred to herein, a tandem repeat is a repeated sequence being found in a natural protein. A preferred tandem repeat is the tandem repeat sequence of MUC1.

In a preferred embodiment, at least 3 of the 5 potential sites for O-glycosylation of the tandem repeat are glycosylated and carrying either Tn or STn.

In another preferred embodiment, all five potential sites for O-glycosylation are carrying either Tn or STn.

We have demonstrated that the capability of the immunogenic glycopeptide to induce an immune response against the MUC1 protein is dependent on the degree of glycosylation of the immunogenic glycopeptide. Thus, a higher degree of glycosylation induces a stronger immune response. However, in some situations, a strong immune response may not be desired or necessary. E.g. for the generation of hybridoma cells producing antibodies that bind the MUC1 protein or aberrantly glycosylated MUC1 protein, the immune response need not necessarily be strong.

In a preferred embodiment, the GSTA (SEQ ID NO. 7) motif is present in a tandem repeat, wherein the sequence of the tandem repeat is selected from the group consisting of:
  a) VTSAPDTRPAPGSTAPPAHG (SEQ ID NO.1)
  b) naturally occurring variants of SEQ ID NO:1 with at least 75% similarity to SEQ ID NO:1
  c) artificial variants of SEQ ID NO:1 wherein said artificial variants are prepared by one or more conservative substitutions and wherein said artificial variants have at least 75% similarity to SEQ ID NO:1
  d) truncated fragments of SEQ ID NO:1 with 1-3 deleted amino acids SEQ ID NO:1 is the tandem repeat sequence of MUC 1 as present in humans.

Naturally occurring variants of SEQ ID NO:1 with at least 75% similarity to SEQ ID NO:1 is to be understood as variants of SEQ ID NO:1 that exist in nature. In other embodiments, it is preferred that naturally occurring variants have a degree of similarity selected from the group consisting of 80%, 85%, 90% and 95%.

Artificial variants of SEQ ID NO:1 as referred to herein are variants that have been prepared artificially e.g. by genetic engineering or chemical synthesis. Typically, artificial variants will be prepared using one or more conservative substitutions.

Truncated fragments of SEQ ID NO:1 has been truncated at either the N-terminal end of the peptide, the C-terminal end of the peptide or at both ends. In a preferred embodiment, the length of the truncation (number of deleted amino acid residues) is selected from the group consisting of: 1 residue, 2 residues, 3 residues, 4 residues, 5 residues, 6 residues, 7 residues, 8 residues, 9 residues and 10 residues. When the truncated fragment is truncated in both ends, the minimum length of the peptide will be selected from the group consisting of: 9 amino acid residues, 10 amino acid residues, 11 amino acid residues, 12 amino acid residues, 13 amino acid residues, 14 amino acid residues, 15 amino acid residues and 16 amino acid residues.

In a preferred embodiment, the GSTA (SEQ ID NO. 7) motif is present in a truncated fragment of SEQ ID NO:1 or variants thereof having a degree of similarity of at least 70% relatively to the truncated fragment.

Conservative substitutions as referred to herein are substitutions of one amino acid residue with another amino acid residue of like charge, size or hydrophobicity.

Preferred conservative substitutions are those wherein one amino acid is substituted for another within the groups of amino acids indicated herein below:

Amino acids having polar side chains (Asp, Glu, Lys, Arg, His, Asn, Gln, Ser, Thr, Tyr, and Cys,)
Amino acids having non-polar side chains (Gly, Ala, Val, Leu, Ile, Phe, Trp, Pro, and Met)
Amino acids having aliphatic side chains (Gly, Ala Val, Leu, Ile)
Amino acids having cyclic side chains (Phe, Tyr, Trp, His, Pro)
Amino acids having aromatic side chains (Phe, Tyr, Trp)
Amino acids having acidic side chains (Asp, Glu)
Amino acids having basic side chains (Lys, Arg, His)
Amino acids having amide side chains (Asn, Gln)
Amino acids having hydroxy side chains (Ser, Thr)
Amino acids having sulfur-containing side chains (Cys, Met),
Neutral, weakly hydrophobic amino acids (Pro, Ala, Gly, Ser, Thr)
Hydrophilic, acidic amino acids (Gln, Asn, Glu, Asp), and
Hydrophobic amino acids (Leu, Ile, Val)

Particular preferred conservative amino acids substitution groups are: valine-leucine-isoleucine, phenylalanine-tyrosine, lysine-arginine, alanine-valine, and asparagine-glutamine.

Various methods of determining the degree of similarity or the percent similarity between two peptides are known. When referring to degree of similarity or percent similarity herein, the following method is used:

The peptides to be compared are aligned optimally. An alignment program may aid in performing the best alignment. When the two sequences are aligned, a score can be assigned that indicate the degree of similarity between the two peptides. Positions with identical amino acid residues are assigned a score of 1. Positions with conservative substitutions are assigned a score of 0.5. Gaps introduced to optimize the alignment are assigned a score of 0.25. Non-conservative substitutions are assigned a score of 0. After scoring all positions over the window of comparison, the score is summarized and normalized against the length of the window of comparison. The normalized value is the percent similarity or degree of similarity as used herein. Consider e.g. a tandem repeat peptide with 1 non-conservative substitution and 3 conservative substitutions relatively to SEQ ID NO:1. The score of the peptide will be 16+(3*0.5)=17.5. The corresponding percent similarity will be 17.5/20=87.5%.

In a preferred embodiment, the glycosylation pattern of the tandem repeat is selected from the group consisting of:

$VT^{Tn}SAPDTRPAPGST^{Tn}APPAHG-$ (SEQ ID NO. 1)

$VT^{Tn}SAPDTRPAPGS^{Tn}T^{Tn}APPAHG-$ (SEQ ID NO. 1)
VT$^{Tn}$SAPDT$^{Tn}$RPAPGS$^{Tn}$T$^{Tn}$APPAHG- (SEQ ID NO. 1)
VT$^{Tn}$S$^{Tn}$APDTRPAPGS$^{Tn}$T$^{Tn}$APPAHG- (SEQ ID NO. 1)
VT$^{Tn}$S$^{Tn}$APDT$^{Tn}$RPAPGS$^{Tn}$T$^{Tn}$APPAHG- (SEQ ID NO. 1)
VT$^{STn}$SAPDTRPAPGST$^{STn}$APPAHG- (SEQ ID NO. 1)
VT$^{STn}$SAPDTRPAPGS$^{STn}$T$^{STn}$APPAHG-

-continued (SEQ ID NO. 1)
VT$^{STn}$SAPDT$^{STn}$RPAPGS$^{STn}$T$^{STn}$APPAHG- (SEQ ID NO. 1)
VT$^{STn}$S$^{STn}$APDTRPAGS$^{STn}$T$^{STn}$APPAHG- (SEQ ID NO. 1)
VT$^{STn}$S$^{STn}$APDT$^{STn}$RPAPGS$^{STn}$T$^{STn}$APPAHG- In an even more preferred embodiment, the glycosylation pattern of the tandem repeat is selected from the group consisting of:

(SEQ ID NO. 1)
VT$^{Tn}$SAPDTRPAPGS$^{Tn}$T$^{Tn}$APPAHG- (SEQ ID NO. 1)
VT$^{Tn}$S$^{Tn}$APDT$^{Tn}$RPAPGS$^{Tn}$T$^{Tn}$APPAHG- (SEQ ID NO. 1)
VT$^{STn}$SAPDTRPAPGS$^{STn}$T$^{STn}$APPAHG- (SEQ ID NO. 1)
VT$^{STn}$S$^{STn}$APDT$^{STn}$RPAPGS$^{STn}$T$^{STn}$APPAHG-

An advantageous effect has been reported by combining more than one tandem repeat for immunization. Thus, in a preferred embodiment, the immunogenic glycopeptide comprises more than one tandem repeat, such as more than 2 tandem repeats, such as more than 3 tandem repeats, such as more than 4 tandem repeats, such as more than 5 tandem repeats, such as more than 6 tandem repeats, such as more than 7 tandem repeats, such as more than 8 tandem repeats such as more than 9 tandem repeats, and such as more than 10 tandem repeats.

Further, in a preferred embodiment, the immunogenic glycopeptide is coupled to a suitable carrier selected from the group consisting of: human serum albumin, keyhole limpet hemocyanin (KLH), thyroglobulin, ovalbumin, influenza hemagglutinin, PADRE polypeptide, malaria circumsporozite (CS) protein, hepatitis B surface antigen (HBSAgI9-2s), Heat Shock Protein (HSP) 65, *Mycobacterium tuberculosis*, cholera toxin, cholera toxin mutants with reduced toxicity, diphtheria toxin, CRM 97 protein that is cross-reactive with diphtheria toxin, recombinant Streptococcal C5a peptidase, *Streptococcus pyogenes* ORF1224, *Streptococcus pyogenes* ORF1664, *Streptococcus pyogenes* ORF2452, *Chlamydia pneumoniae* ORF T367, *Chlamydia pneumoniae* ORF T858, Tetanus toxoid or HIVgp120T1.

Coupling to a carrier is done to increase the potency of the immunological peptide.

Pharmaceutical Composition

Since the immunogenic glycopeptide can induce a cancer specific immune response, another aspect of the present invention is a pharmaceutical composition comprising the immunogenic glycopeptide.

In a preferred embodiment, the pharmaceutical composition is a cancer vaccine for treatment or prevention of breast cancer, ovarian cancer, pancreatic cancer, or lung cancer.

Method of Treating or Preventing Cancer

Another aspect of the invention is a method of treating or preventing cancer comprising administrating the aforementioned pharmaceutical composition comprising the immunogenic glycopeptide. In doing so, a cancer specific immune response will be raised.

Antibodies

Other aspects of the present invention are antibodies prepared using the immunogenic glycopeptide, methods for preparation of said antibodies and use of said antibodies in therapy and diagnosis.

Thus, another aspect of the present invention is a method for the preparation of hybridoma cells, which secrete monoclonal antibodies specific for the immunogenic glycopeptide characterized in that:

a suitable mammal is immunized with the immunogenic glycopeptide, antibody-producing cells of said mammal are fused with cells of a continuous cell line, the hybrid cells obtained in the fusion are cloned, and cell clones secreting the desired antibodies are selected.

Still another aspect is a monoclonal antibody selected from the group consisting of:

A monoclonal antibody produced by the hybridoma cells prepared by the method described above A monoclonal antibody prepared by molecular display techniques, such as mRNA display, ribosome display, phage display and covalent display against the immunogenic glycopeptide.

Traditionally, monoclonal antibodies have been prepared using hybridoma technology. However, alternative techniques such as mRNA display, ribosome display, phage display and covalent display are now available. These are all display techniques where a peptide library is selected against the immunogenic glycopeptide. Such techniques can e.g. be used to identify humanized or fully human antibodies.

In a preferred embodiment, the monoclonal antibody binds MUC1 on cancer cells but not MUC1 on a non-malignant counterpart.

In another preferred embodiment, the monoclonal antibody binds preferentially to MUC1 that is aberrantly glycosylated and expressed on cancer cells.

In still another embodiment, the monoclonal antibody binds to or at least interacts directly with the O-glycosylated GSTA (SEQ ID NO. 7) motif of the immunogenic glycopeptide. Our data strongly indicate that antibodies binding to the O-glycosylated GSTA (SEQ ID NO. 7) motif are indeed cancer specific and that cancer specificity may lie in this interaction. Not intended to be bound by theory, we believe that antibodies that bind to or interact with the O-glycosylated GSTA (SEQ ID NO. 7) motif will display cancer specificity. In particular so, if they bind or interact with the O-glycosylated GSTA (SEQ ID NO. 7) motif carrying an O-glycosylation at the S-residue and the T-residue at the same time.

In a preferred embodiment, the antibody prepared using the immunogenic glycopeptide is humanized or fully human, such as to decrease the immunogenicity of the antibody in humans. This is typically desirable if the antibody is used as a therapeutic.

However, in some situations a rapid clearance may be desired, wherefore also non-humanized antibodies are of interest as therapeutics. One such situation can e.g. be when administering antibodies coupled to toxins or radioisotopes. Such conjugated antibodies should either find their target rapidly or be cleared as they have a general toxic effect. One embodiment of the invention is conjugated antibodies.

Another embodiment of the invention is the monoclonal antibody, 5E5, secreted by the hybridoma deposited at the European Collection of Cell Cultures (ECACC), Centre for Emergency Preparedness and Response of The Health Protection Agency, Porton Down, Salisbury SP4 OJG, a depository in compliance with the Budapest Treaty of 1977, on Sep. 19, 2006, under accession number STHM1 06092102.

Another embodiment of the invention is the monoclonal antibody, 2D9, secreted by the hybridoma deposited at ECACC, Centre for Emergency Preparedness and Response of The Health Protection Agency, Porton Down, Salisbury SP4 OJG, a depository in compliance with the Budapest Treaty of 1977, on Sep. 19, 2006, under accession number: STHM2 06092101.

The aforementioned deposits were made by Mads Agervig Tarp on Sep. 19, 2006. The deposit was given the following reference number: Q6847.

Another aspect of the invention is the use of a monoclonal antibody, prepared using the immunogenic glycopeptide, as a medicament.

In a preferred embodiment, the medicament is used for treatment or prevention of cancer.

Still another aspect is the use of a monoclonal antibody, prepared using the immunogenic glycopeptide, for the preparation of a medicament for the treatment or prevention of cancer.

Since monoclonal antibodies prepared using the immunogenic glycopeptide display cancer specificity, a further aspect of the invention is a pharmaceutical composition comprising the monoclonal antibody prepared using the immunogenic glycopeptide.

In a preferred embodiment, the antibody of the pharmaceutical composition is conjugated to a toxin or a radionuclide.

Still another aspect of the invention is a method of determining whether an individual has cancer or is at risk of developing cancer comprising the steps of:

Providing a sample from the individual

Contacting the antibody prepared using the immunogenic glycopeptide with the sample Removing antibodies not interacting with the sample From the antibodies interacting with the sample, determine whether the individual has cancer or is at risk of developing cancer Still another aspect of the invention is an ex vivo-method of producing a population of autologous antigen presenting cells (APCs), which are capable of inducing effective immune responses against MUC1, comprising the steps of:

providing autologous APCs from a tumor patient contacting the autologous APCs from the tumor patient with an effective amount of the immunogenic glycopeptide of the invention, wherein said contacting is under conditions which allow endocytosis, processing, and MHC class II presentation of fragments of said glycopeptide or fusion molecule by said APCs; and isolating said peptide or fusion molecule fragment-presenting APCs for the purpose of immunotherapeutic application in the patient Still another aspect of the present invention is a method of determining the presence of antibodies binding to the immunogenic glycopeptide, comprising the steps of:

a. Providing a sample comprising human antibodies b. Contacting the sample with a peptide inhibitor and an O-glycan carbohydrate inhibitor c. Further contacting the sample of step b with the glycopeptide d. Quantifying the amount of antibodies interacting with the glycopeptide sample Man has natural antibodies to the Tn, STn and T carbohydrate structures and these appear to be increased in cancer patients. It is believed that such antibodies will react with the corresponding MUC1 glycopeptides similar to the panel of monoclonal anti-Tn, -STn and -T antibodies analyzed. In order to identify novel MUC1 glycopeptide antibodies in human serum, it is therefore necessary to develop assays that can selectively identify glycopeptide specific antibodies without interference from anti-peptide or anti-carbohydrate antibodies.

While not intended to be bound by theory, it is believed that a peptide inhibitor and an O-glycan carbohydrate inhibitor can be used to neutralize cross-reacting antibodies, without affecting antibodies specific for the immunogenic glycopeptide, i.e. antibodies that bind the immunogenic glycopeptide, but not carbohydrates alone or the non-glycosylated peptide. Thus, the presence of antibodies specific for the immunogenic glycopeptide can be detected and even quantified. Since it has been demonstrated that these antibodies are cancer specific, the method can be used for diagnosis and prognosis in relation to cancer.

The sample may be serum, plasma, body fluids such as milk, saliva, mucosal secretions, feces, urine and any antibody preparations hereof.

The peptide inhibitor will typically be a peptide of the same amino acid sequence as the immunogenic glycopeptide, however, without any glycosylations. In another embodiment, the peptide inhibitor comprises fully processed branched core 2 O-glycans, as is typically present in normal cells.

The carbohydrate inhibitor will typically be Tn, STn or T. Also preferred are polyvalent PAA conjugates of the aforementioned carbohydrates. Still in another embodiment, the carbohydrate inhibitor is a monosaccharide such as GalNAc, GlcNAc, Gal, Glc and NeuAc. It will be apparent to the skilled man that other combinations of carbohydrates will have the same effect.

In a preferred embodiment, the method further comprises a step of removing antibodies that interact with the peptide inhibitor and/or with the O-glycan carbohydrate inhibitor.

In still another embodiment, the peptide inhibitor and the O-glycan inhibitor has been immobilized on a solid support, which is used to remove antibodies that interact with the peptide inhibitor and/or with the O-glycan carbohydrate inhibitor.

In still another embodiment, the antibodies binding to the immunogenic glycopeptide, binds to the O-glycosylated GSTA (SEQ ID NO. 7) motif of the immunogenic glycopeptide. As is apparent from the present specification, such antibodies are cancer specific and their presence may indicate that the individual has cancer.

Thus, in another preferred embodiment
a. the sample is provided from an individual that is suspected of having cancer
b. the determined amount of antibodies that interact with the glycopeptide is compared to a standard amount, said standard amount being determined from a control group
c. a determined amount of antibodies above the standard amount is indicative of cancer in the individual
d. a determined amount of antibodies below the standard amount is indicative of the individual not having cancer It is noted that the above described method of determining the presence of antibodies binding to the immunogenic glycopeptide is not necessarily limited to the immunogenic glycopeptide of the present invention. The method should be applicable for detection of antibodies specifically binding (not binding to peptide or carbohydrate alone) to other glycopeptides as well.

FIGURE LEGENDS

FIG. 1. Chemoenzymatic synthesis of multimeric Tn and STn MUC1 glycopeptides:

Synthetic 60-mer MUC1 tandem repeat peptides (VT-SAPDTRPAPGSTAPPAHG)$_{n=3}$ (SEQ ID NO. 1) were glycosylated using site-selective recombinant polypeptide GalNAc-transferases (GalNAc-T2, -T4 and -T11). The sites of GalNAc attachments in MUC1 tandem repeat sequences were strictly controlled as indicated by MALDI-TOF mass spectrometry analysis of MUC1 60-mer tandem repeat peptides glycosylated in vitro with recombinant GalNAc-transferases. GalNAc-T11 was used to add 2 GalNAc residues per tandem repeat, GalNAc-T2 to add 3 residues, and sequential use of GalNAc-T2 and -T4 to add all 5 residues. Sites of attachments were confirmed by mass spectrometry as previously described. Glycosylation with GalNAc-T4 to achieve five GalNAc residues per repeat only allowed 14 in total due to the design of the peptide with the NH$_2$-terminal being too truncated. Further glycosylation of GalNAc residues with sialic acid to form STn was achieved with recombinant murine ST6GalNAc-I. Evaluation of number of sialic acid residues attached by MALDI-TOF may be underestimated due to the labile nature of this sugar linkage. The sialylation is considered complete as evaluated by immunoreactivity pattern with anti-STn (positive) and anti-Tn (negative) monoclonal antibodies. The core 1 T structure was produced using a recombinant β3Gal-transferase. Glycopeptides formed are depicted on top of each MALDI-TOF profile. The mass scale of spectra shown are 5,000-10,000 counts.

Figure 2:
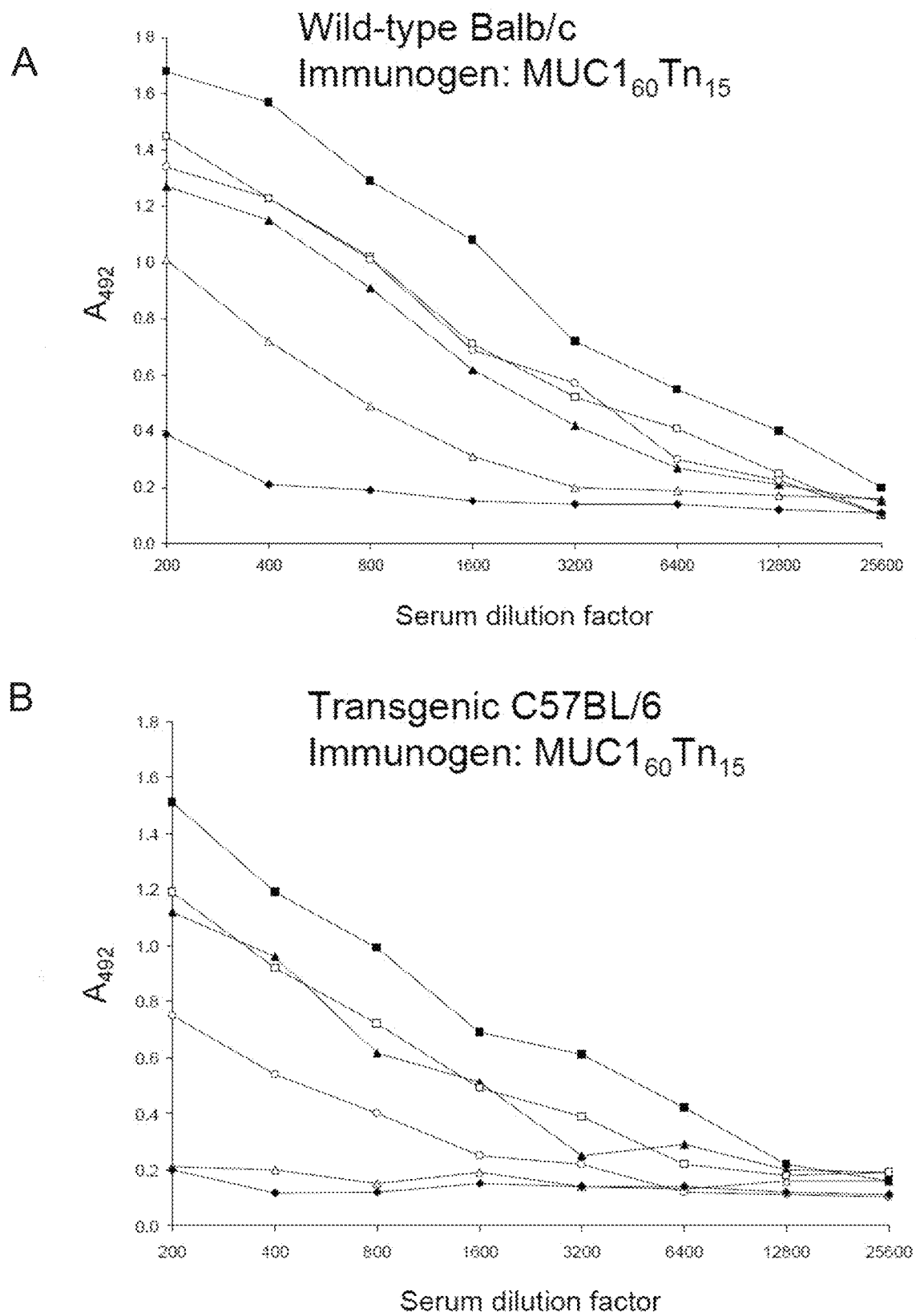
Figure 2:
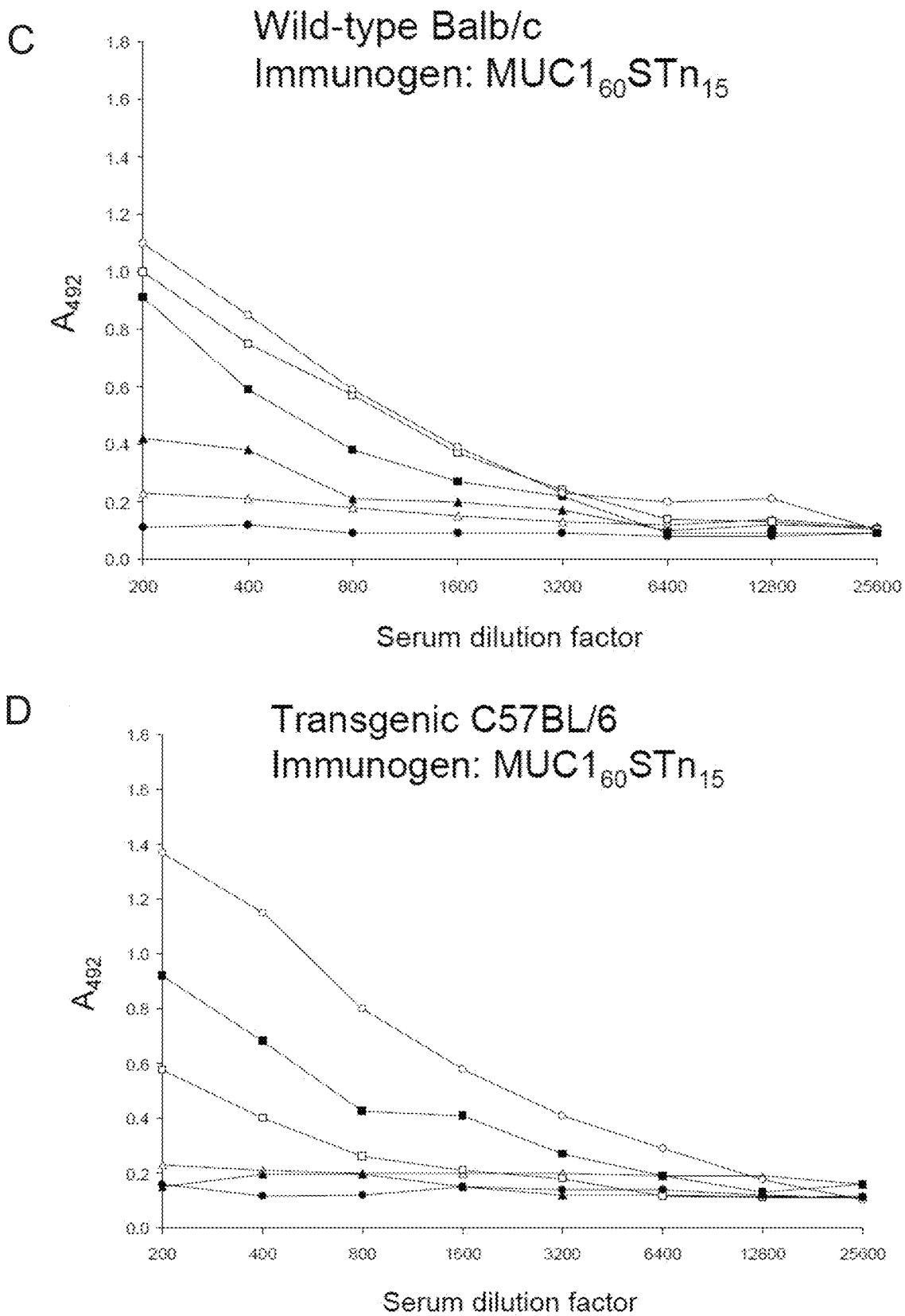

FIG. 2. MUC1 glycopeptides with complete O-glycan attachment are most immunogenic and Tn and STn glycopeptides elicit strong antibody responses in MUC1 transgenic mice.

(a) ELISA assay of serum from one representative (of four) wild-type Balb/c mouse immunized with complete Tn glycosylated MUC1 (MUC1$_{60}$Tn$_{15}$). Designations are as follows: ■=MUC1$_{60}$Tn$_{15}$; □=MUC1$_{60}$Tn$_9$; ○=MUC1$_{60}$STn$_{15}$; ●=OSM (STn); ▲=MUC1$_{60}$Tn$_6$; Δ=MUC1$_{60}$; ▲=AOSM (Tn). Additional peptides tested which gave no reactivity include unglycosylated MUC2, Tn MUC2, and Tn MUC4. (b) ELISA assay of serum from one representative (of four) wild-type mouse immunized with the complete STn glycosylated MUC1 glycopeptide (MUC1$_{60}$Tn$_{15}$). The highest antibody titers were found with the MUC1 glycoform used as immunogen, but considerable reactivity with the other MUC1 glycoforms were found as well. Low reactivity with unglycosylated MUC1 was found in particularly in the Tn immunized mice. Very low levels of anti-Tn and STn hapten antibodies were detected using the mucin OSM (ovine submaxillary mucin with mainly STn glycoform) and AOSM (asialo-mucin with Tn glycoform) as antigens. No reactivity with non-MUC1 peptides or glycopeptides with Tn-glycosylation were found. (c) ELISA assay of serum from one (of four) MUC1.Tg mice immunized with complete Tn glycosylated MUC1 (MUC1$_{60}$Tn$_{15}$). (d) ELISA assay of serum from one (of four) MUC1.Tg mice immunized with the complete STn glycosylated MUC1 glycopeptide (MUC1$_{60}$STn$_{15}$). The highest antibody titers were found with the MUC1 glycoform used as immunogen, but considerable reactivity with the other MUC1 glycoforms was found as well. No reactivity was detected with unglycosylated MUC1 as well as the mucins OSM (STn) and AOSM (Tn) and non-MUC1 Tn glycopeptides.

Figure 3:
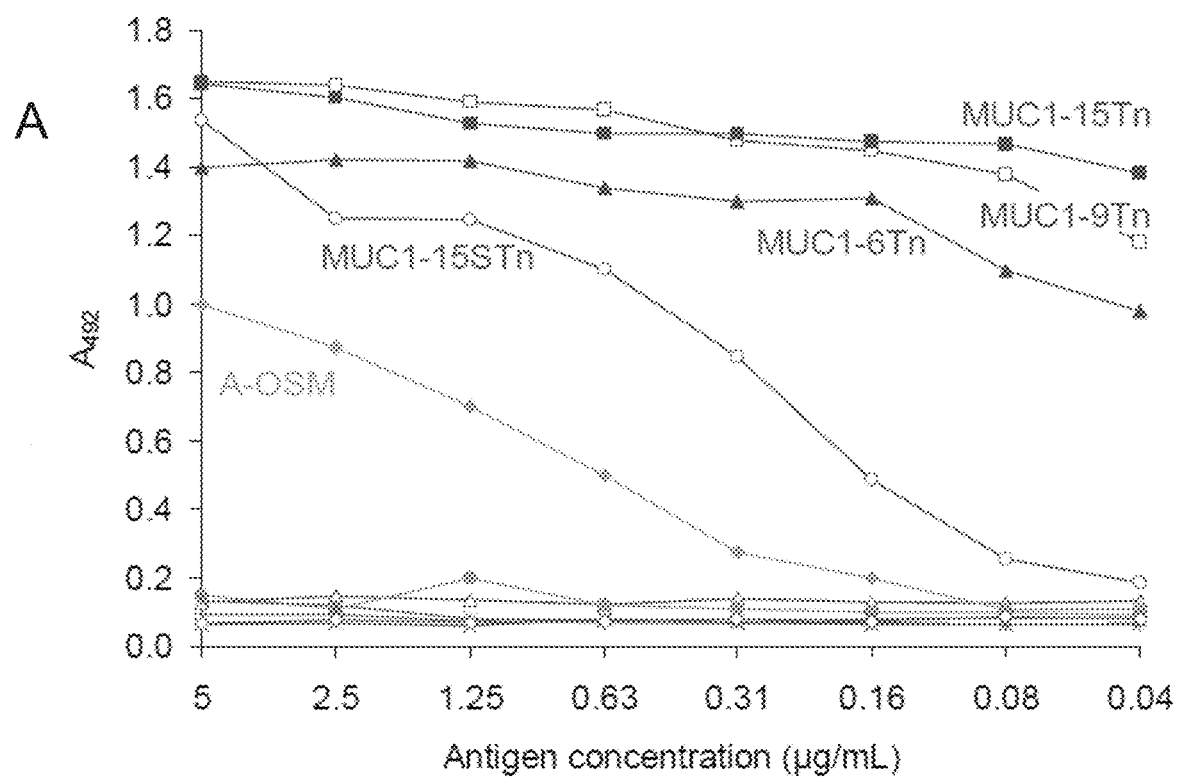
Figure 3:
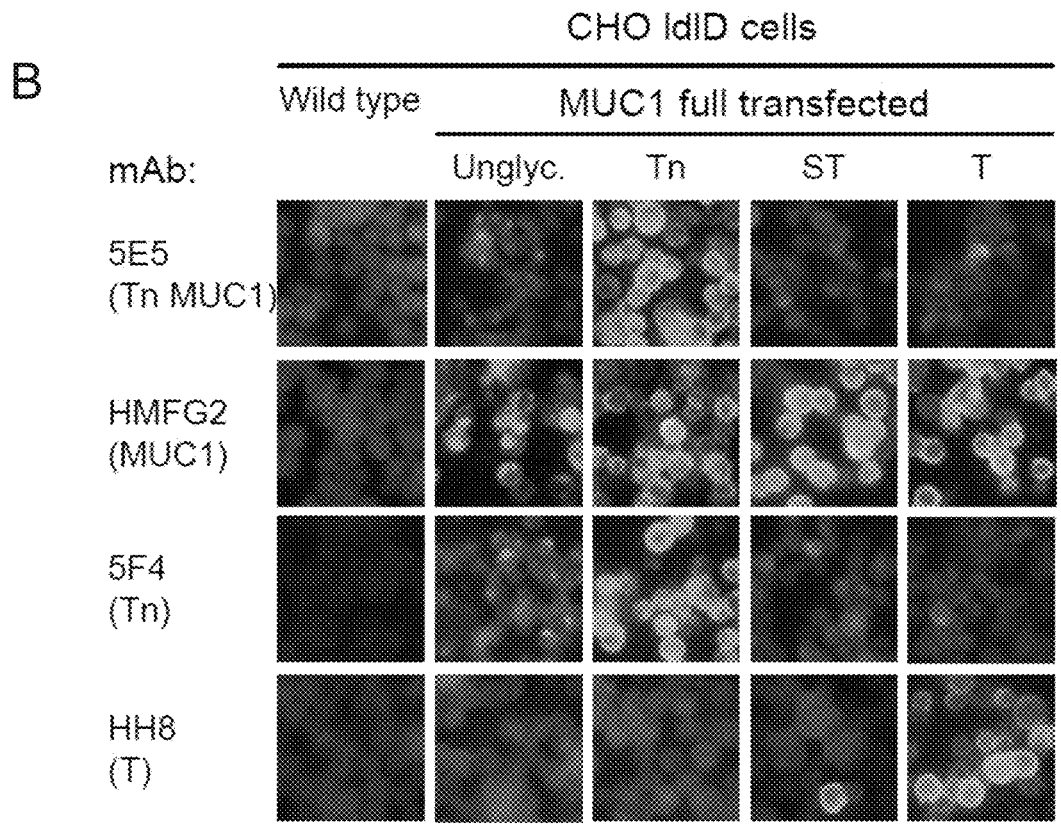
Figure 3:
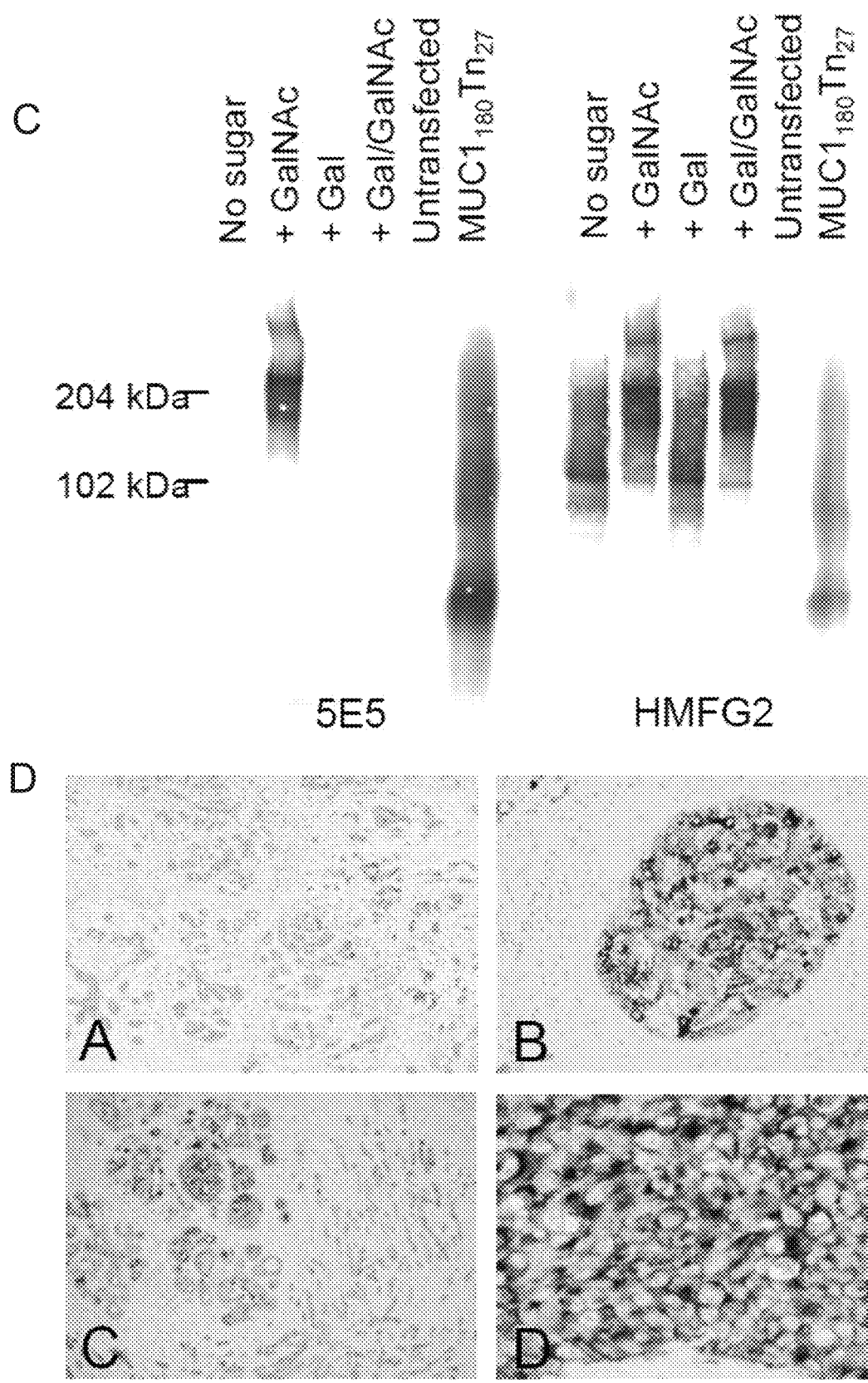

FIG. 3. Characterization of a monoclonal antibody 5E5 that mimics the immune response elicited in wild type and MUC1.Tg mice immunized with Tn MUC1.

(a) ELISA assay with monoclonal antibody 5E5 shows strong reactivity with all glycoforms of the MUC1 tandem repeat sequence, but no reactivity with the unglycosylated MUC1 peptide. Weak reactivity was also observed with AOSM, but no reactivity was detected with other Tn glycopeptides. Designations as in FIG. 2. Negative control peptides include unglycosylated MUC2, Tn MUC2, Tn MUC4Tn$_1$ and Tn MUC4Tn$_3$. (b) Immunofluorescence staining with Mab 5E5 (top row) showing reactivity with CHO ldlD cells expressing the Tn MUC1 glycoform, no reactivity with cells expressing unglycosylated MUC1, ST MUC1 or T MUC1 (after pretreatment with neuraminidase) glycoforms as well as wild type CHO ldlD cells. Control antibodies to MUC1 (HMFG2), Tn (5F4) and T (HH8) were included to confirm the expression of MUC1 and the respective glycoforms Tn, T, and ST as indicated (c) SDS-PAGE Western blot analysis of culture medium of CHO ldlD cells secreting different MUC1-glycoforms. Monoclonal antibody 5E5 exhibits strict specificity for the secreted Tn MUC1 glycoform, while HMFG2 reacts with all glycoforms as well as unglycosylated MUC1. (d) Immunohistochemical staining of breast tissues with monoclonal antibody 5E5. Primary breast infiltrating ductal carcinoma grade II stained with 5E5. Note that surrounding normal tissue is negative (A). Ductal carcinoma in situ stained with 5E5 (B). Grade II ductal carcinoma showing areas of DCIS. Both infiltrating and DCIS are staining with 5E5 (C). Primary breast infiltrating ductal carcinoma grade III stained with 5E5 (D).

Figure 4:
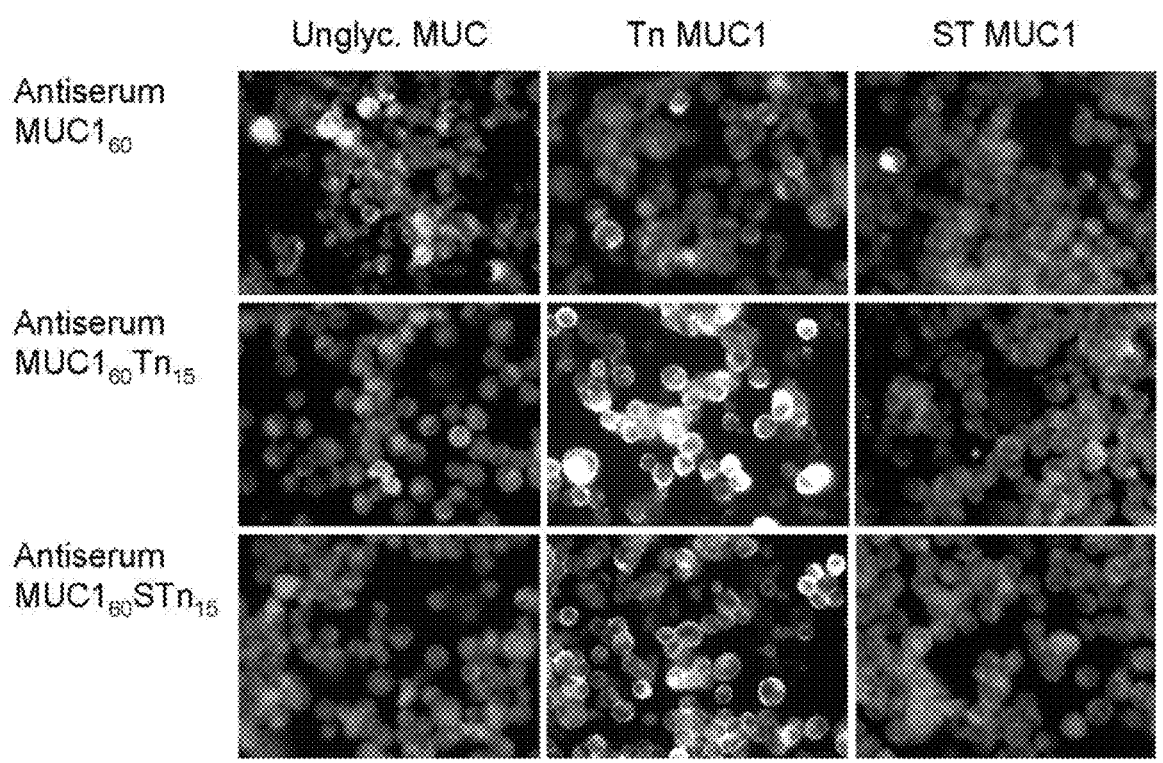
Figure 4:
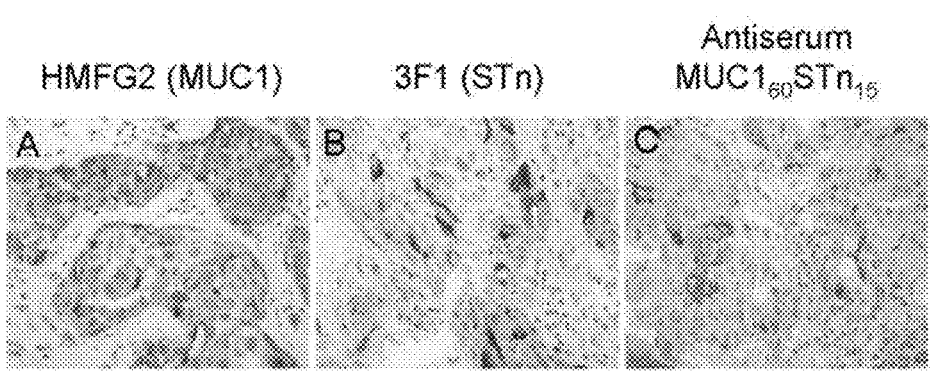

FIG. 4. MUC1.Tg mice immunized with MUC1 Tn and STn glycopeptides produce MUC1 glycopeptide specific responses restricted to cancer-associated MUC1 glycoforms.

(a) Sera from MUC1.Tg mice immunized with MUC1 Tn or STn glycopeptides reacted with Tn MUC1 but not unglycosylated or T/ST glycoforms of MUC1 expressed in CHO ldlD cells. Sera from Tg mice immunized with unglycosylated MUC1 reacts preferentially, but weakly with CHO ldlD cells expressing unglycosylated MUC1. (b) Sera from Tg mice immunized with MUC1 glycopeptides recognize MUC1 expressed by cancer cells. Immunohistochemical staining of a primary breast carcinoma expressing both STn (B) and MUC1 (A) (determined by monoclonal antibodies HB-STn and HMFG2) with serum from one Tg mouse immunized with MUC160STn15 (C).

FIG. 5. Glycopeptides used for characterization of MAb specificities.

Biotinylated 60-mer glycopeptides: (VTSAPDTRPAPG-STAPPAHG)n=3 (SEQ ID NO. 1)

Prefix numbers indicate number of O-glycans in peptides. Tn: GalNAcα1-O-Ser/Thr; STn: NeuAcα2-6GalNAcα1-O-Ser/Thr; T: Galβ1-3GalNAcα1-O-Ser/Thr; ST: NeuAcα2-3Galβ1-3GalNAcα1-O-Ser/Thr; core 3: GlcNAcβ1-3GalNAcα1-O-Ser/Thr.

Biotinylated 25-mer valine-substituted glycopeptides: TAP25V9:

(TAPPAHGVTSAPDTRPAPGSVAPPA) (SEQ ID NO. 11) Valine-substituted in position 9; TAP25V21: Valine-substituted in position 21; 2Tn-TAP25V9 and 2Tn-TAP25V21 are glycosylated with Tn (GalNAcα-O-Ser/Thr) in the indicated positions.

21-mer: (AHGVTSAPDTRPAPGSTAPPA) (SEQ ID NO. 12) Synthetic glycopeptides with a single Tn (GalNAcα1-O-Ser/Thr) or T (Galβ1-3GalNAcα1-O-Ser/Thr) glycan in the indicated positions.

Figure 6:
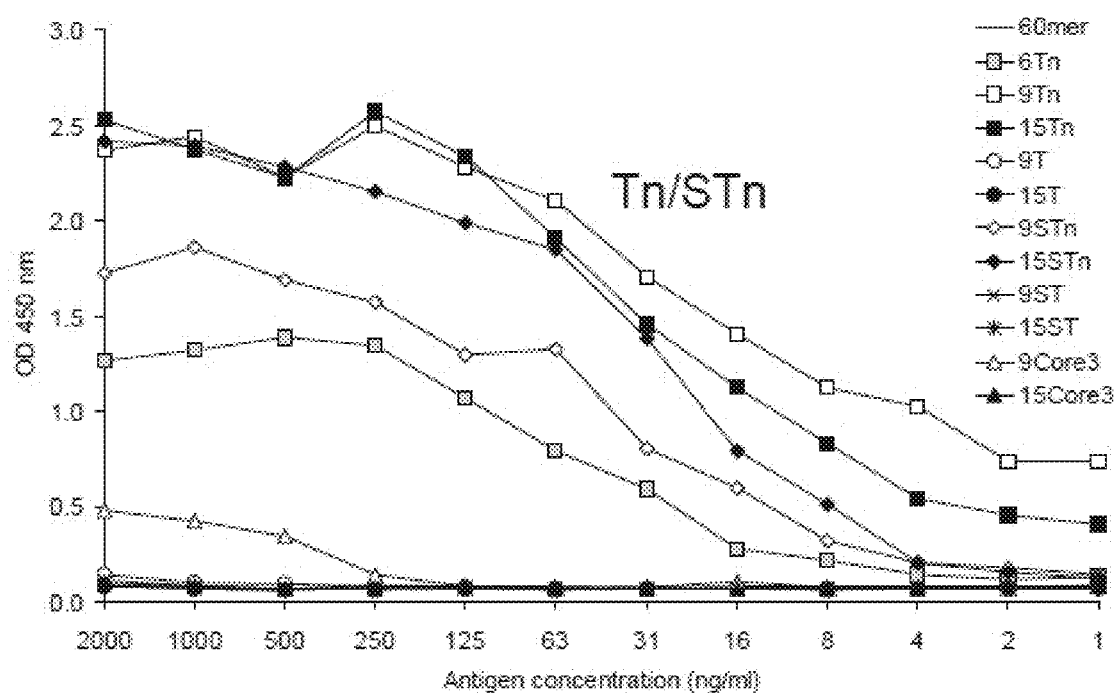
Figure 6:
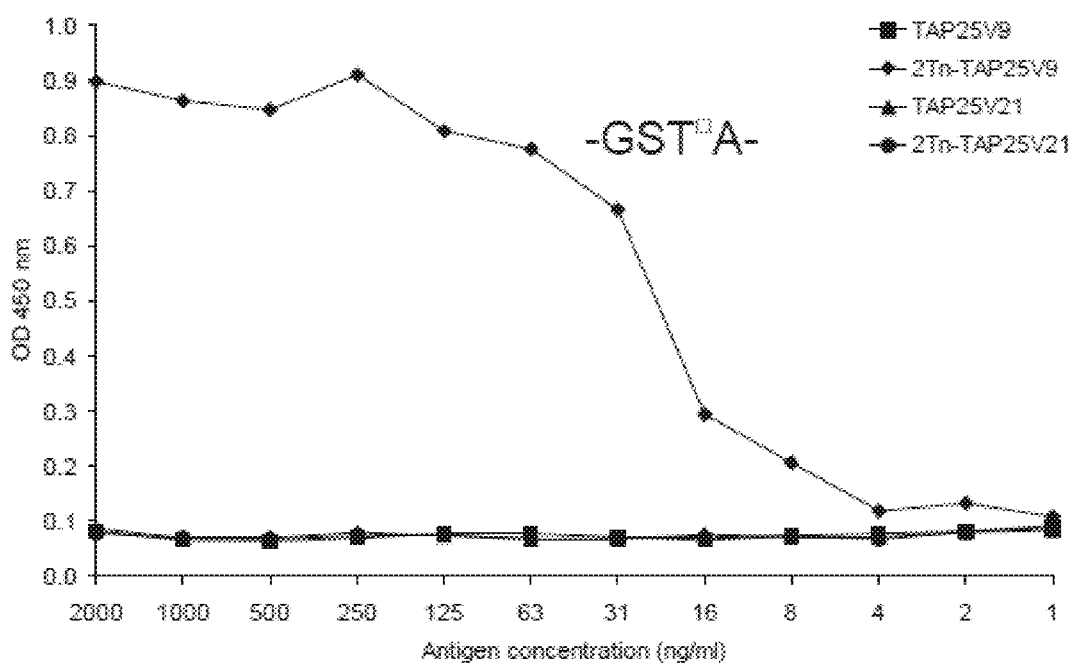
Figure 6:
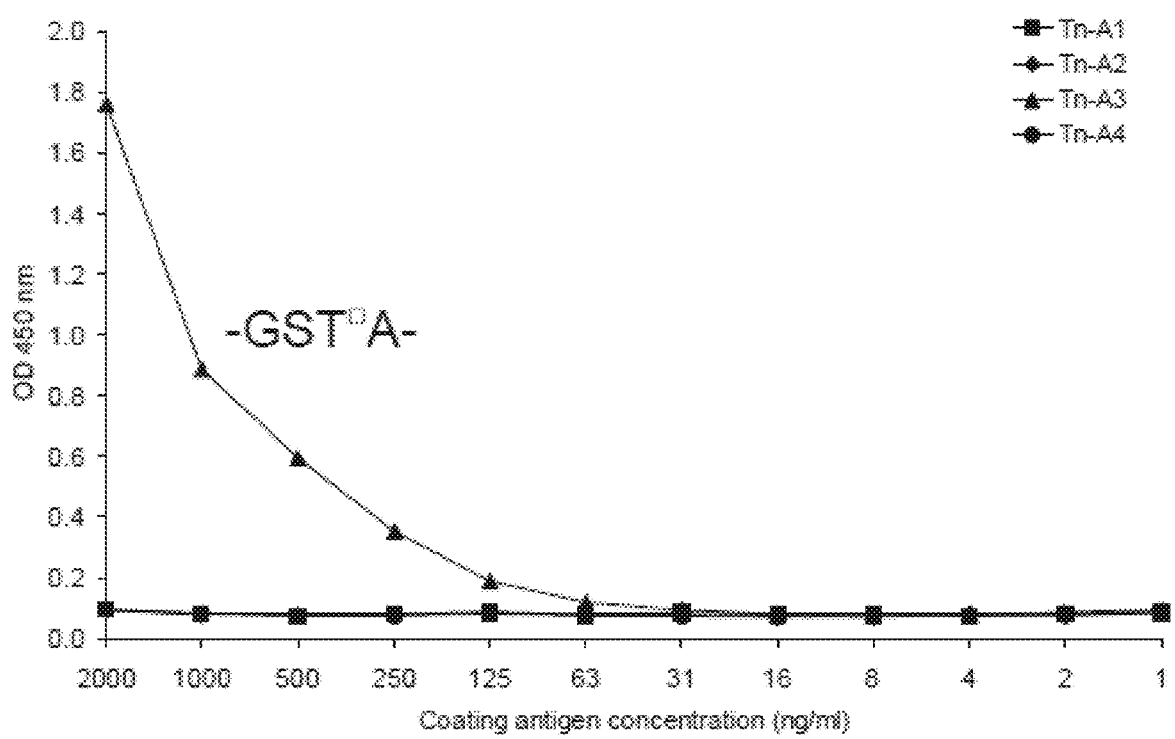
Figure 6:
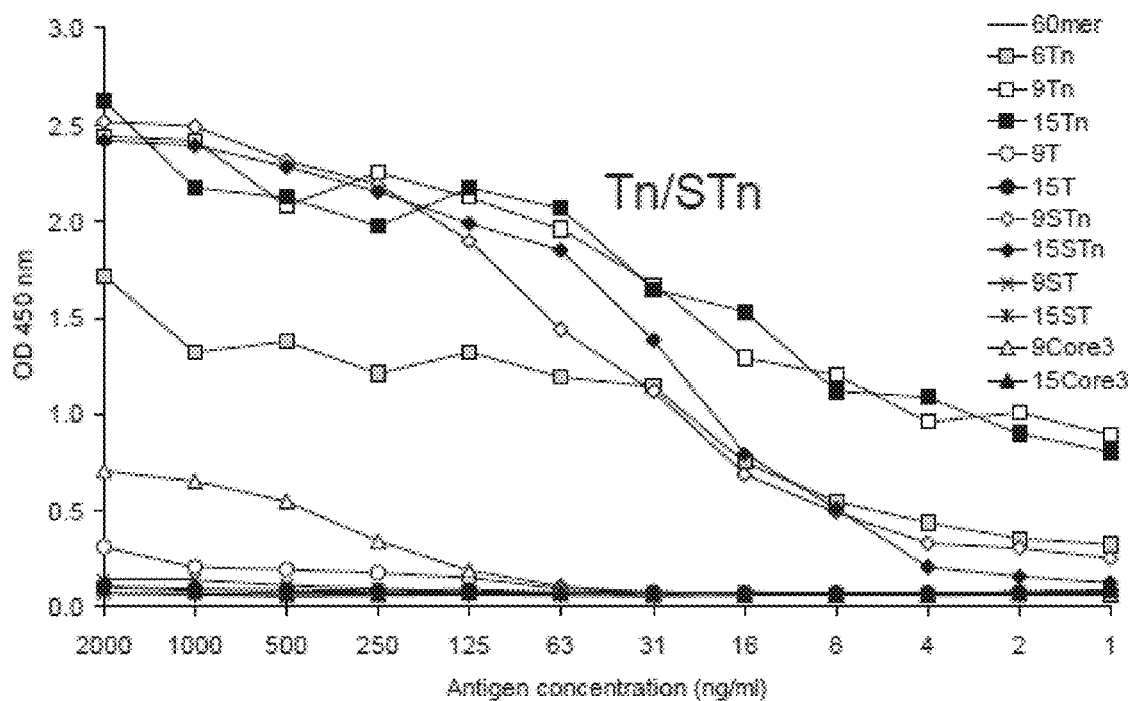
Figure 6:
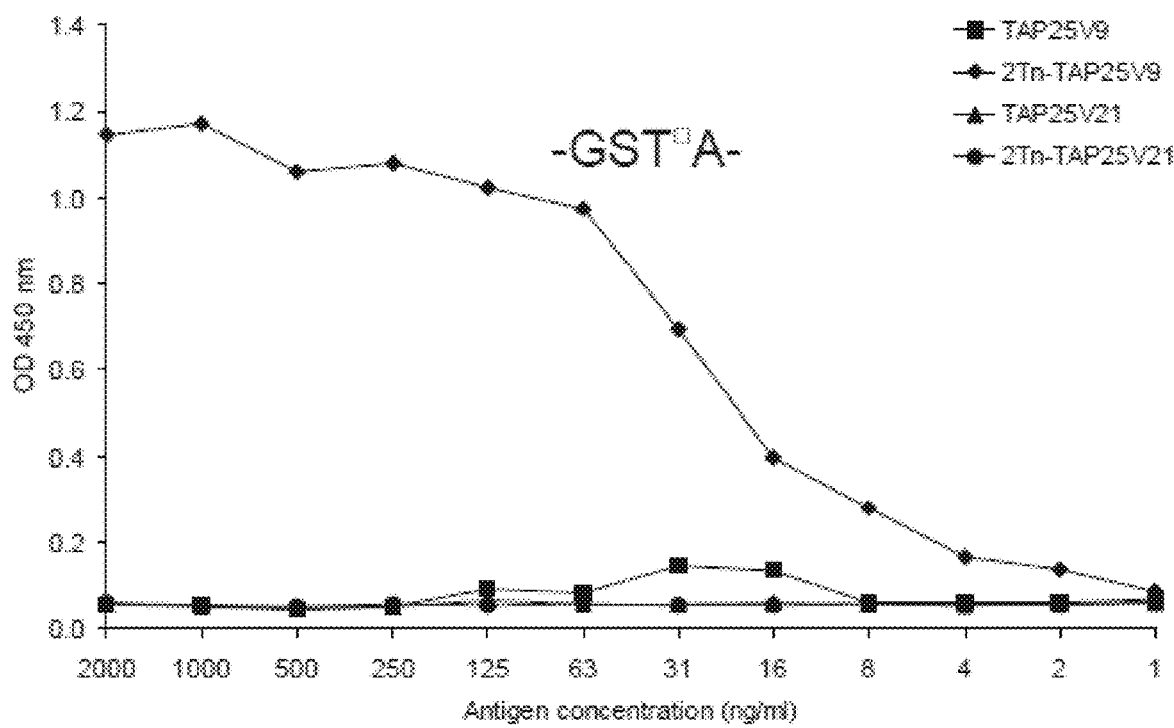
Figure 6:
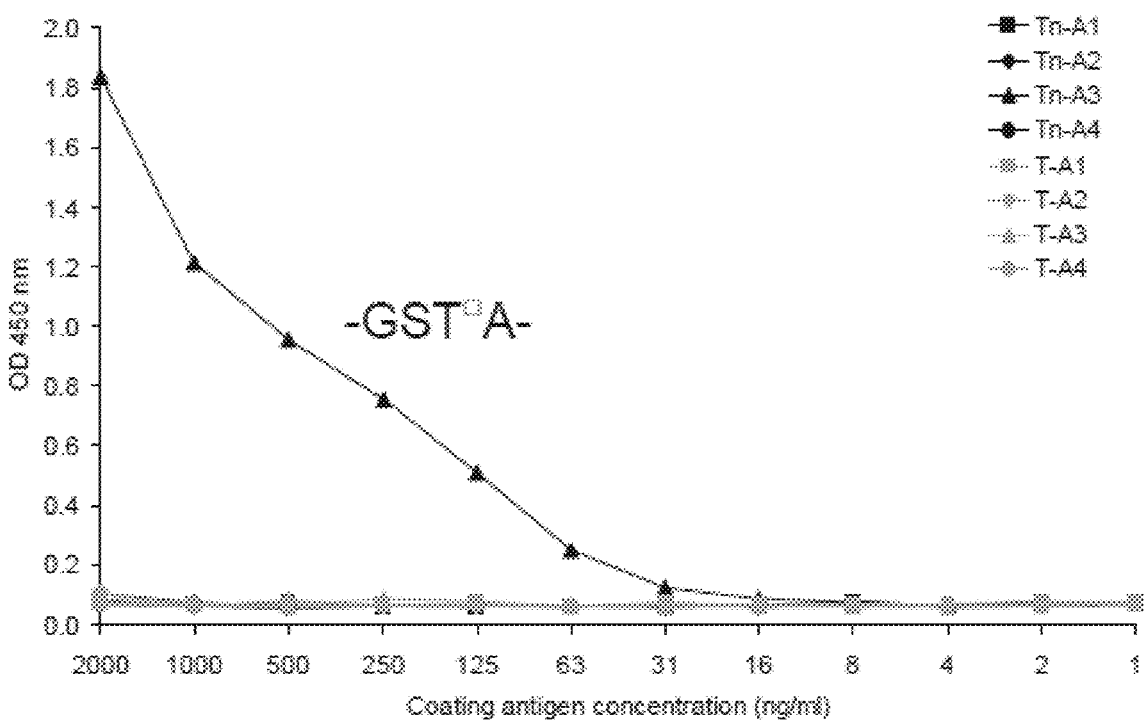

FIG. 6. Specificity analysis of MAbs 2D9 and 5E5 by ELISA.

Panels A and D: Reactivity of MAbs 2D9 and 5E5 with biotinylated 60-mer glycopeptides by capture ELISA (FIG. 1). Strong reactivity is seen for both MAbs with high-density Tn and STn glycoforms.

Panels B and E: Reactivity of MAbs 2D9 and 5E5 with biotinylated valine-substituted 25-mer glycopeptides by capture ELISA. Strong reactivity is seen for both MAbs with the peptide Tn-glycosylated at Thr in the GSTA region. ☐ indicates Tn-glycosylation.

Panels C and F: Reactivity of MAbs 2D9 and 5E5 with 21-mer glycopeptides glycosylated with a single Tn or T glycan by direct binding ELISA. Strong reactivity is seen for both MAbs with the peptide Tn-glycosylated at Thr in the GSTA region. ☐ indicates Tn-glycosylation.

Controls for 25- and 21-mer peptides are shown with MAb 5E10 in FIG. 5, panels B and C.

Figure 7:
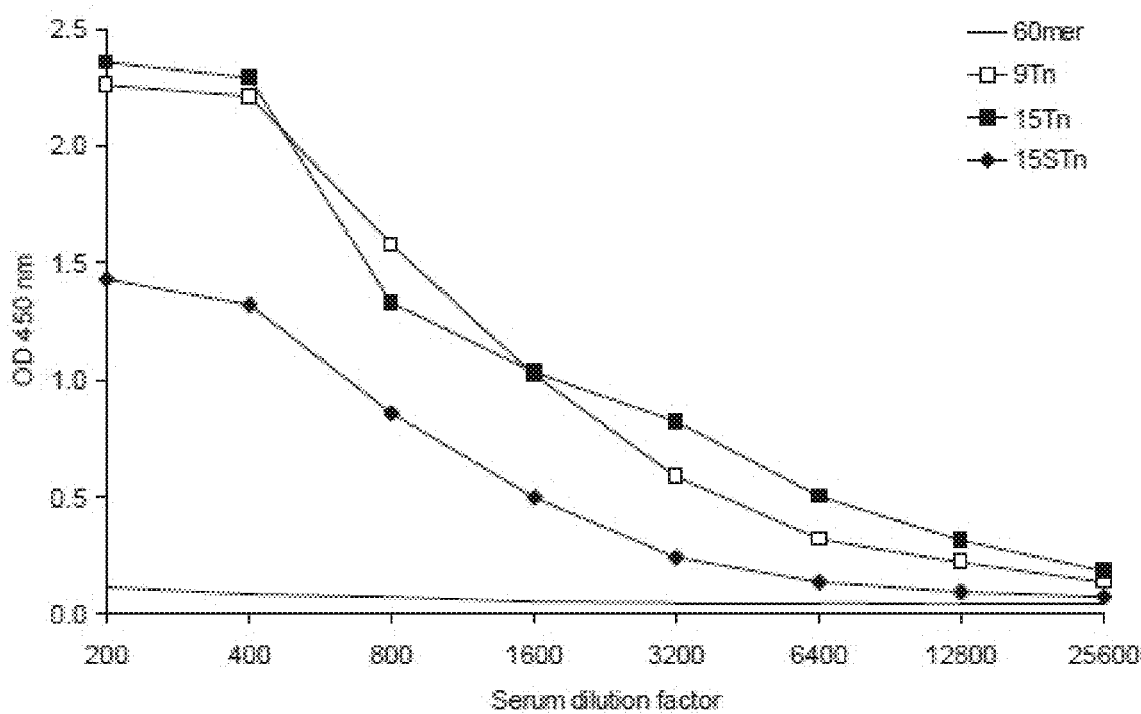
Figure 7:
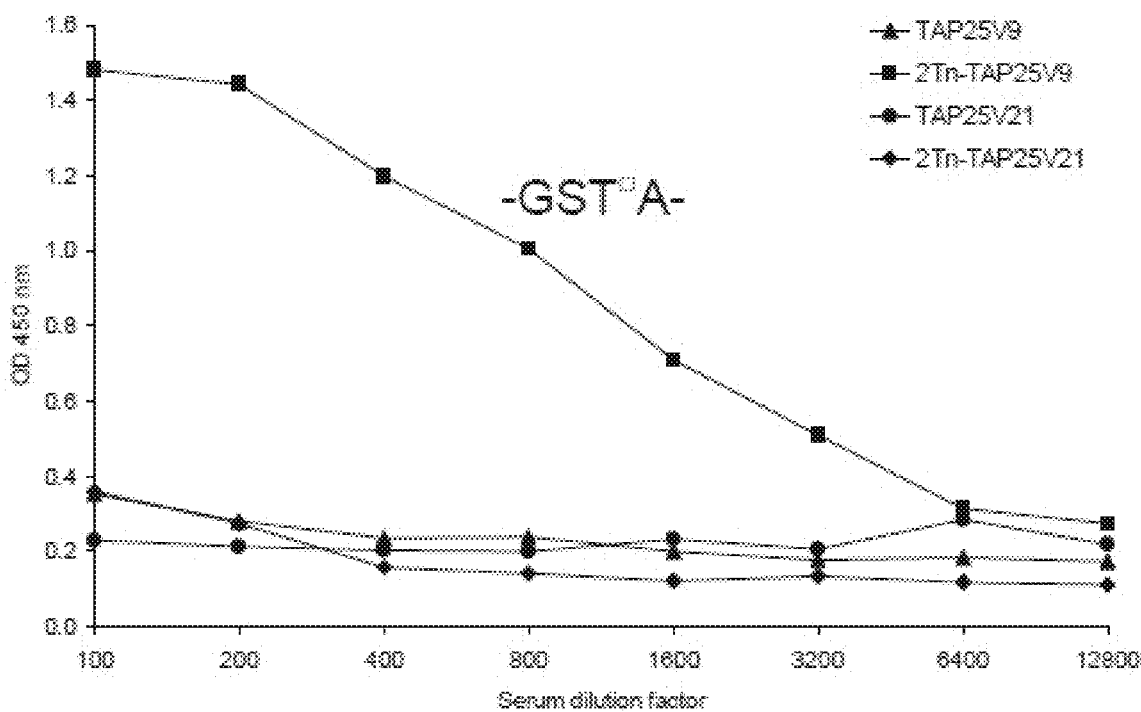

FIG. 7. Specificity analysis of serum from MUC1 transgenic mice immunized with 15Tn-MUC1 60-mer glycopeptide.

Panel A: Reactivity with 60-mer glycopeptides by direct binding ELISA. Strong reactivity is seen with glycopeptides with three or five Tn glycans per tandem repeat. Lower reactivity is seen with the fully STn-glycosylated peptide. No reactivity is seen with the unglycosylated peptide.

Panel B: Reactivity with biotinylated valine-substituted 25-mer glycopeptides by capture ELISA. Strong reactivity is seen with the peptide Tn-glycosylated at Thr in the GSTA region. ☐ indicates Tn-glycosylation.

Figure 8:
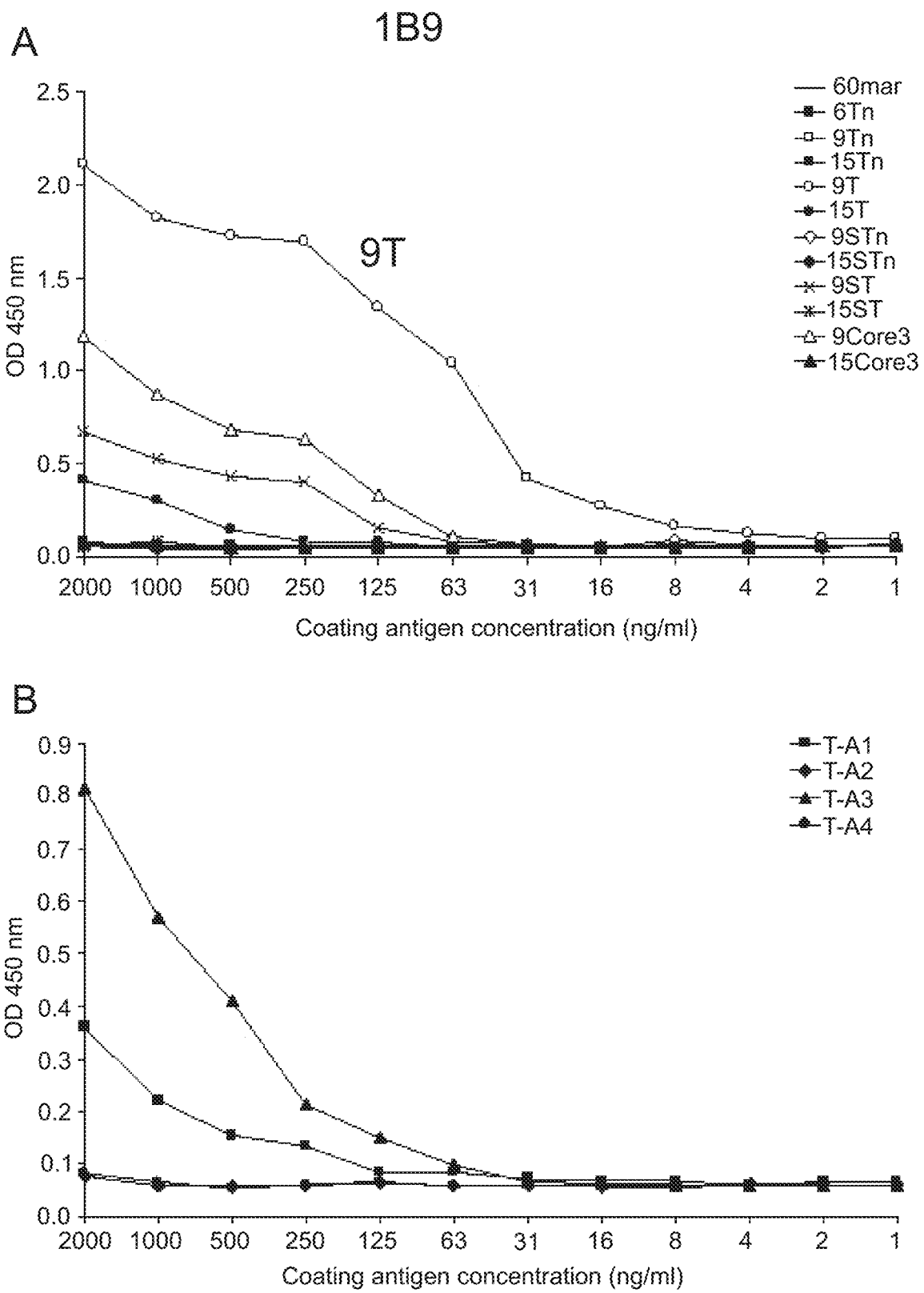
Figure 8:
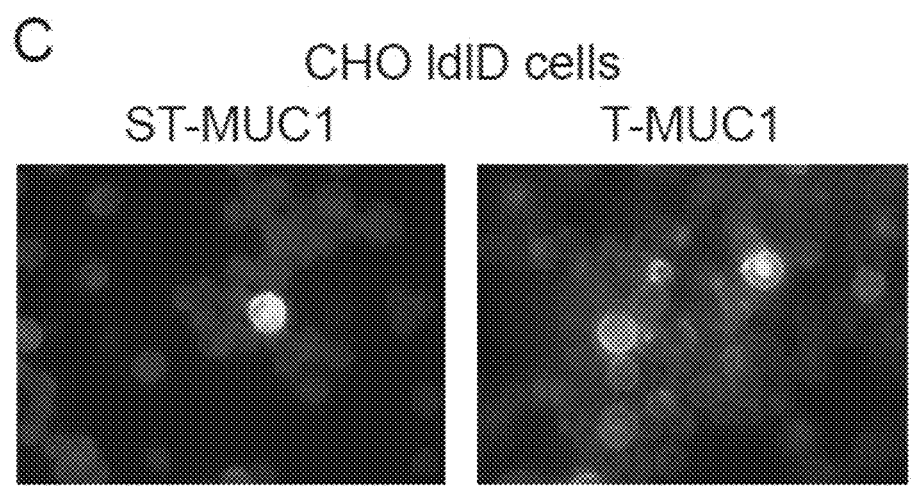
Figure 8:
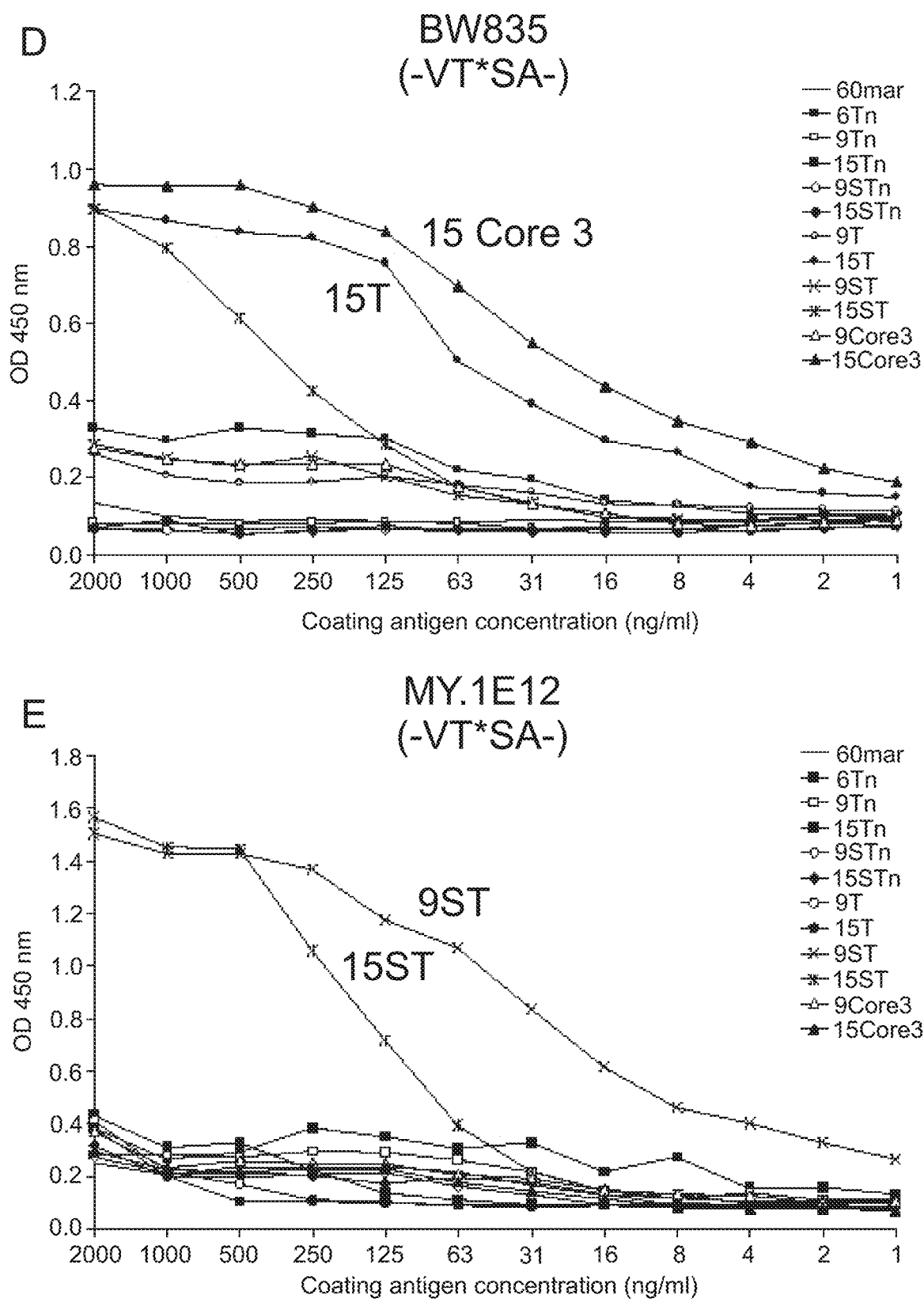

FIG. 8. Specificity analysis of MAbs 1B9, BW835 and MY.1E12 by ELISA.

Panel A: Reactivity of MAb 1B9 with biotinylated 60-mer glycopeptides. Reactivity is also seen with core 3 and ST glycans (see text for details).

Panel B: Reactivity of MAb 1B9 with biotinylated valine-substituted 25-mer glycopeptides. Reactivity is seen with glycopeptides with T glycans at Thr in the GSTA region and Thr in the VTSA (SEQ ID NO. 6) region.

Panel C: Reactivity of MAb 1B9 with CHO ldlD cells grown in Gal/GalNAc. 1B9 reacts with approximately 2% of the cells expressing ST-MUC1 (no neuraminidase treatment), whereas it reacts with approximately 20% of cells presenting T-MUC1 (neuraminidase treated).

Panel D: Reactivity of MAb BW835 with biotinylated 60-mer glycopeptides. Published epitope listed in parenthesis where o indicates T-glycosylation. Strong reactivity is seen with the glycopeptides with five T or core 3 glycans per tandem repeat. Lower reactivity is observed with five ST glycans per tandem repeat.

Panel E: Reactivity of MAb MY.1E12 with biotinylated 60-mer glycopeptides. Published epitope listed in parenthesis where * indicates ST-glycosylation. Strong reactivity is seen with the glycopeptide with five ST glycans per tandem repeat. Lower reactivity is observed with three ST glycans per tandem repeat.

Figure 9:
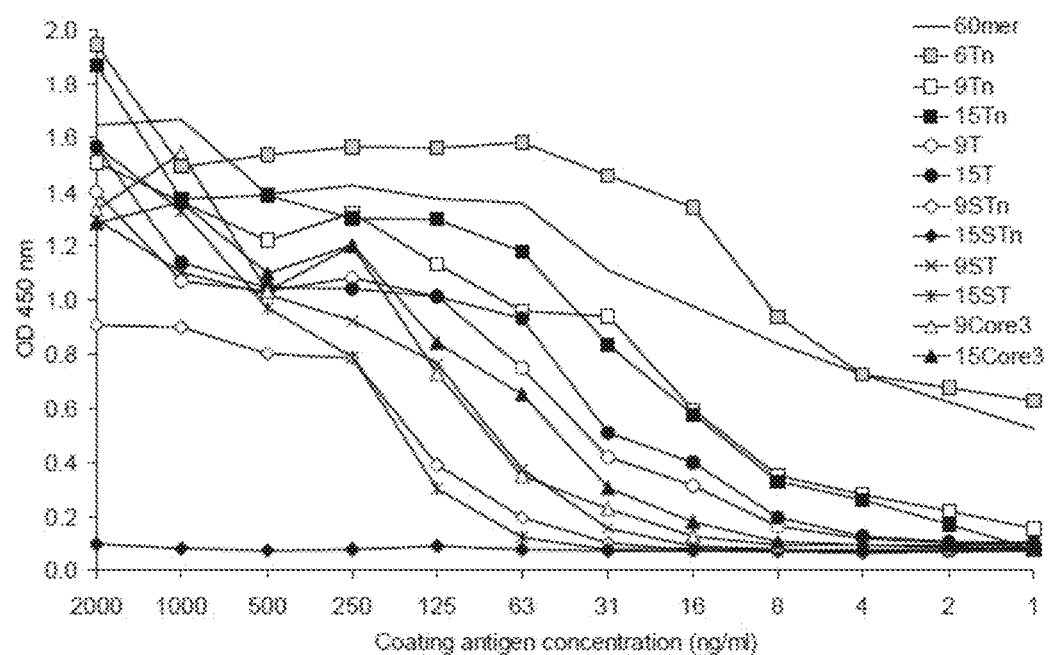
Figure 9:
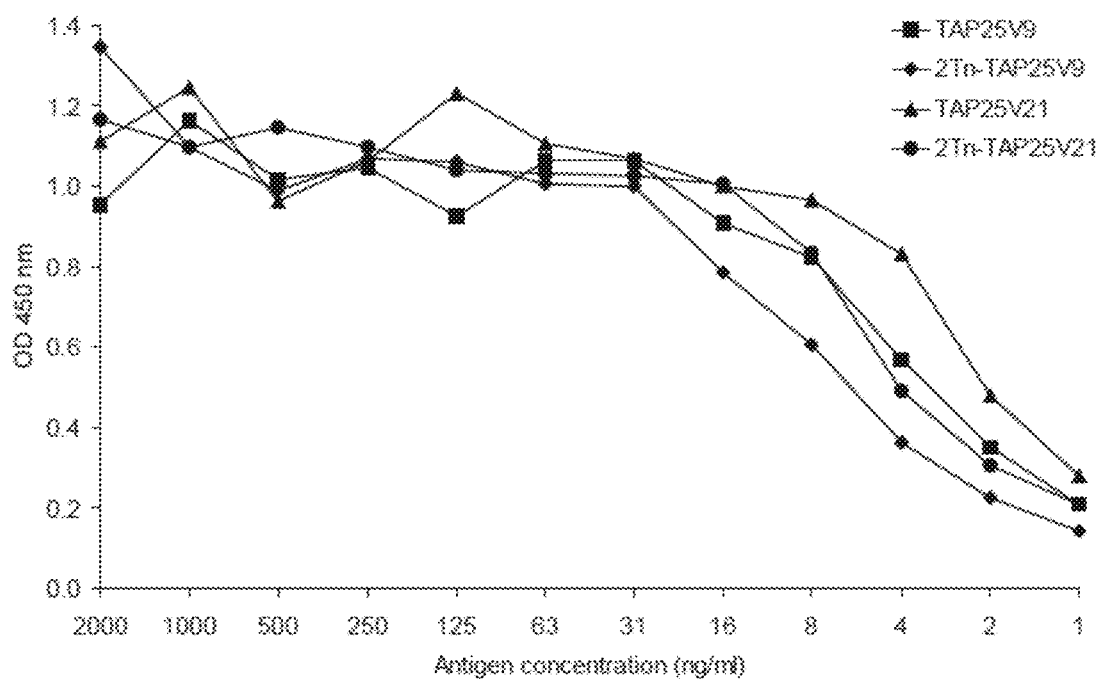
Figure 9:
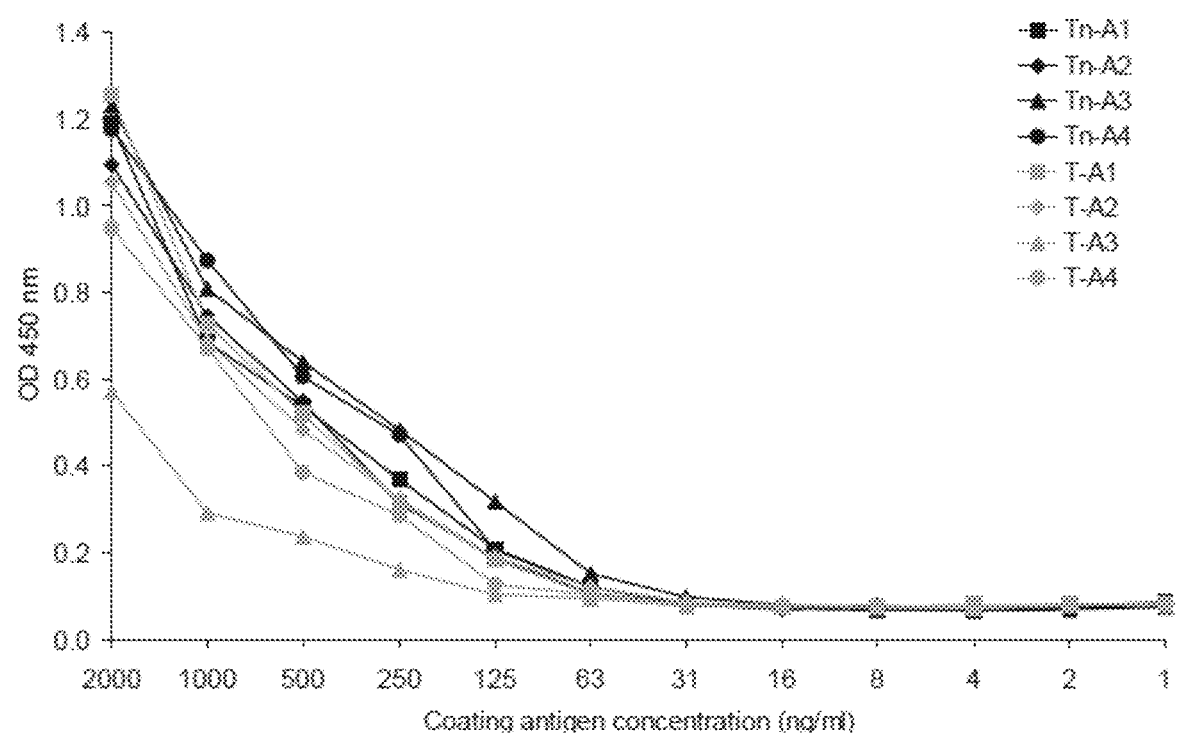
Figure 9:
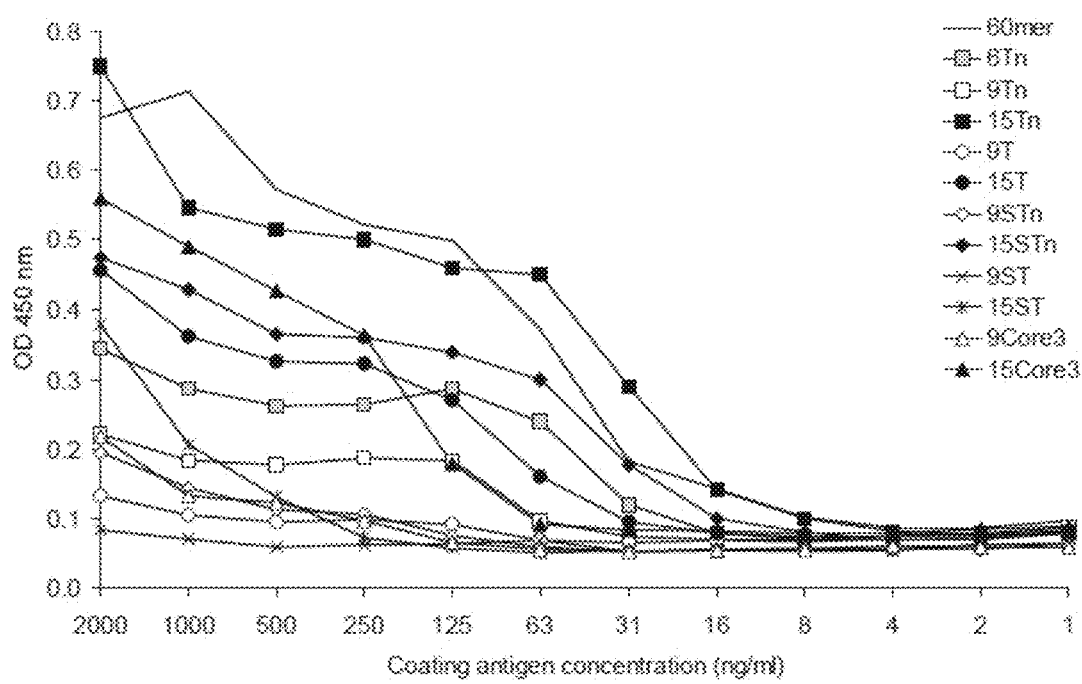
Figure 9:
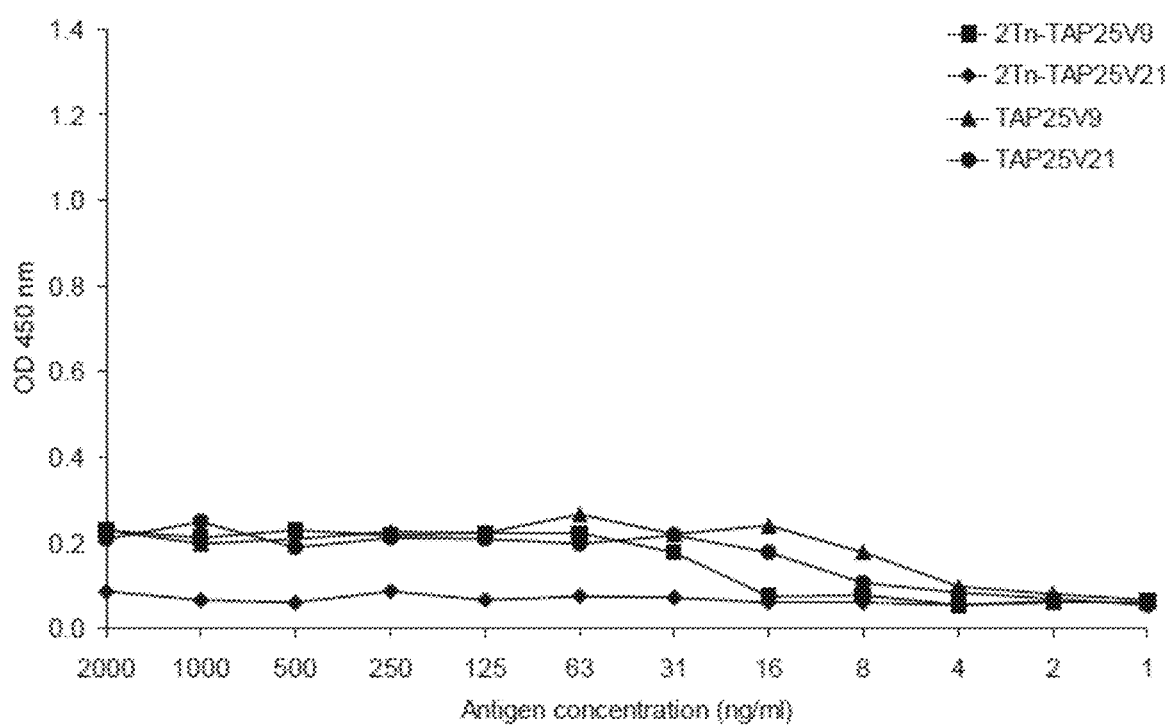
Figure 9:
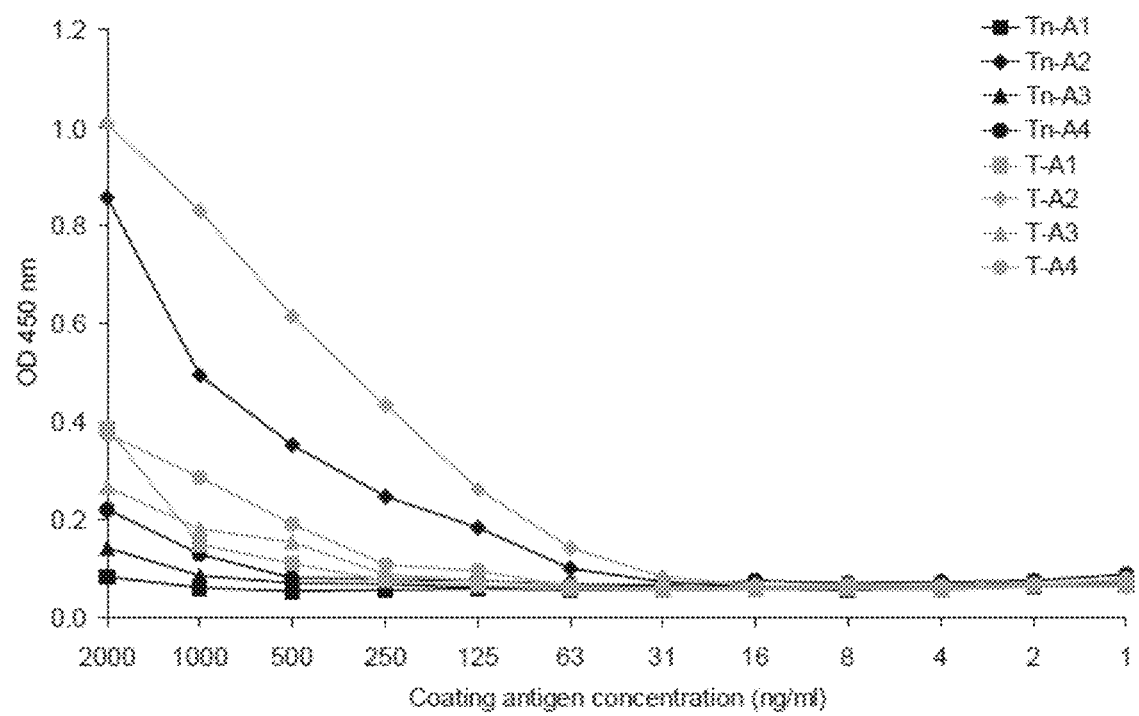

FIG. 9. Specificity analysis of MAbs 5E10 and SM3 by ELISA.

Panel A: Reactivity of MAb 5E10 with biotinylated 60-mer glycopeptides. Reactivity is seen with all tested peptides except when fully glycosylated with the STn glycan. Preference is seen for unglycosylated and Tn glycoforms, followed by T and ST glycoforms. Lowest reactivity is seen with the glycopeptide with three STn glycans per tandem repeat.

Panel B: Reactivity of MAb 5E10 with biotinylated valine-substituted 25-mer glycopeptides. Strong reactivity is seen with all peptides independent on Tn-glycosylation.

Panel C: Reactivity of MAb 5E10 with 21-mer glycopeptides glycosylated with a single Tn or T glycan. Relatively strong reactivity is seen with all glycopeptides with exception of the peptide with a T glycan at Thr in the PDTR (SEQ ID NO. 4) region.

Panel D: Reactivity of MAb SM3 with biotinylated 60-mer glycopeptides. Strongest reactivity is seen with unglycosylated peptide or peptides with five O-glycans per tandem repeat. The glycoforms of preference are Tn, STn, core 3, T, and ST in the mentioned order.

Panel E: Reactivity of MAb SM3 with biotinylated valine-substituted 25-mer glycopeptides. Weak reactivity is seen with the unglycosylated peptides and where the Thr in the GSTA (SEQ ID NO. 7) region is Tn-glycosylated. No reactivity is seen with the glycopeptide glycosylated in the Thr in the VTSA (SEQ ID NO. 6) region.

Panel F: Reactivity of MAb SM3 with 21-mer glycopeptides glycosylated with a single Tn or T glycan. Strongest reactivity is seen with glycopeptides with T- or Tn-glycosylation at Thr in the PDTR (SEQ ID NO. 4) region. Low reactivity is seen with the remaining T-glycosylated and some of the Tn-glycosylated glycopeptides.

EXAMPLES

Example 1

Materials and Methods

Chemoenzymatic Synthesis of Multimeric Tn and STn MUC1 Glycopeptides

MUC1 60-mer (VTSAPDTRPAPGSTAPPAHG)n=3 (SEQ ID NO. 1) peptide was synthesized as originally reported by Fontenot. Control peptides used were derived from tandem repeat of MUC2 (PTTTPISTTTMVTPTPTPTC) (SEQ ID NO. 8) and MUC4 (CPLPVTDTSSASTGHATPLPV) (SEQ ID NO. 9). Peptides were glycosylated in vitro using purified recombinant human glycosyltransferases polypeptide GalNAc-T2, GalNAc-T4, and GalNAc-T11. The GalNAc substituted peptides were subsequently sialylated using purified recombinant mouse ST6GalNAc-I. GalNAc glycosylation of the peptides was performed in a reaction mixture (1 mg peptide/ml) containing 25 mM cacodylate buffer (pH 7.4), 10 mM $MnCl_2$, 0.25% Triton X-100, and 2 mM UDP-GalNAc. Glycosylation of 1 mg 60-mer peptide with 2 GalNAc per TR (MUC160Tn6) was obtained using GalNAc-T11. Incorporation of 3 GalNAc per TR (MUC160Tn9) was obtained using GalNAc-T2. Substitution of all five putative O-glycosylation sites in the MUC1 TR (MUC160Tn15) was performed using MUC160Tn9 as substrate in a reaction with GalNAc-T4. Sialylation was performed in a reaction mixture (1 mg peptide/ml) containing 20 mM Bis-Tris buffer (pH 6.5), 20 mM EDTA, 1 mM dithiothreitol and 2 mM CMP-NANA (Sigma). Glycosylation was monitored using nano-scale reversed-phase columns (Poros R3, PerSeptive Biosystem) and MALDI-TOF mass spectrometry. The glycopeptides were purified by HPLC on a Zorbax 300SB-C3 column (9.4 mm×25 cm) in an 1100 Hewlett Packard system using 0.1% TFA and a gradient of 0-80% acetonitrile. Quantification and estimation of yields of glycosylation reactions were performed by comparison of HPLC peaks by uv 210 absorbance using 10 μg weighed peptide as standard. GalNAc-glycosylation of peptides generally yielded 80-90% recovery, while the sialylation step was more variable with yields from 60-80%. Purified glycopeptides were characterized by MALDI-TOF mass spectrometry on a Voyager DE or Voyager DE Pro MALDI time-of-flight mass spectrometer (PerSeptive Biosystems Inc., Framingham, Mass.) equipped with delayed extraction. The MALDI matrix was 2,5-Dihydroxybenzoic acid 10 g/L (Aldrich, Milwaukee, Wis.) dissolved in 2:1 mixture of 0.1% trifluoroacetic acid in 30% aqueous acetonitrile. Samples dissolved in 0.1% trifluoroacetic acid to a concentration of approximately 1 pmol/μl were prepared for analysis by placing 1 μl of sample solution on a probe tip followed by 1 μl of matrix. All mass spectra were obtained in the linear mode. Data processing was carried out using GRAMS/386 software.

Immunization Protocol

Glycopeptides were coupled to keyhole limpet hemocyanin (KLH) (Pierce, Rockford, Ill.) using glutaraldehyde. Efficiency of conjugation was assessed by analyzing the reaction by size exclusion chromatography on a PD-10 column using anti-MUC1 ELISA of fractions. Essentially all reactivity was found was found with the excluded fraction and insignificant reactivity in the included fractions expected to contain peptides. Further evaluation included comparative titration analysis of the KLH conjugate with the corresponding glycopeptide in ELISA. Both analyses indicated that the conjugation was near complete, which should result in a KLH to glycopeptide ratio of 1:300. MUC1 transgenic mice (MUC1.Tg) homozygous for the transgene expression were originally developed on an H2-k background. Subsequently, these mice have been backcrossed onto a Balb/c strain for 15 generations to give a pure Balb/c (H2-d) background (Graham and Taylor-Papadimitriou, unpublished data). Female Balb/c wild type and MUC1.Tg mice were injected subcutaneously with 10 or 15 μg of (glyco)peptide in a total volume of 200 μl (1:1 mix with Freunds adjuvant, Sigma). Mice received four immunizations 14 days apart, and blood samples were obtained by tail or eye bleeding 1 week following the third and fourth immunization.

Generation of Mouse Monoclonal Anti-Tn-MUC1 Antibody 5E5.

A monoclonal antibody was produced as described previously from a wild type Balb/c mouse immunized with the fully GalNAc-glycosylated 60-mer MUC1 glycopeptide coupled to KLH. Screening was based on glycopeptide ELISA assays followed by immunocytology with breast cancer cell lines (MCF7, T47D, MTSV1-7) and immunohistology with breast cancer tissues. Selection was based on reactivity pattern similar to total sera of the same mouse.

ELISA Assays

Enzyme-linked immunosorbent assays (ELISA) were performed using 96-well MaxiSorp plates (Nunc, Denmark). Plates were coated overnight at 4° C. with 1 μg/ml of glycopeptides in bicarbonate-carbonate buffer (pH 9.6), blocked with 5% BSA in PBS, followed by incubation with sera (diluted in PBS) or monoclonal antibodies for 2 hours at room temperature. Bound antibodies were detected with peroxidase-conjugated rabbit anti-mouse immunoglobulins (Dako, Denmark) or isotype specific antibodies peroxidase-conjugated goat anti-mouse IgM, IgG1, IgG2a, IgG2b, or IgG3 (Southern Biotechnology Associates, USA). Plates were developed with O-phenylenediamine tablets (Dako, Denmark) and read at 492 nm. Control antibodies included anti-MUC1 antibodies HMFG2 and SM3 and anti-carbohydrate antibodies 5F4 (Tn) and 3F1 (STn). Control sera included mice immunized with MUC4 mucin peptide linked to KLH.

Cell Lines

The human mammary cell lines MCF7, MTSV1-7, and T47D, and the murine pancreatic carcinoma cell line Panc02 were cultured as previously described. CHO ldlD cells were stably transfected with full coding MUC1 containing 32 tandem repeats and grown with or without addition of Gal/GalNAc as indicated. Confluent cultures of CHO ldlD cells in 6 well plates (Nunc, Denmark) were grown in HAM'S F12 with 10% FCS without GalNAc and Gal, in presence of 1 mM GalNAc, or in the presence of 1 mM GalNAc and 0.1 mM Gal (Sigma Aldrich). The medium was harvested after 48 hours of growth and used for immunoassays. Cells were trypsinized, washed and airdried on coverslides for immunocytology.

SDS-PAGE Western Blot

SDS-PAGE western blot analysis was performed according to manufacturers instructions (4-12% gradient gel, Biowhittaker Molecular Applications). Membranes were blocked in 15% skimmed milk powder (Merck Eurolab), incubated with MAbs 5E5 and HMFG2 overnight at 4° C., followed by incubation with biotinylated goat anti-mouse IgG1 (0.5 µg/ml)(Southern Biotechnology Inc) for 1 hour at room temperature. Membranes were incubated with avidin horseradish peroxidase conjugate (0.36 µg/ml) (Dako) for 30 min at room temperature, followed by 50 mM Tris-HCl buffer (pH 7.6) containing 0.04% 4-chloro-1-naphthol (Sigma) and 0.025% $H_2O_2$.

Immunocytochemistry

Cell lines were fixed for 10 min in ice cold acetone or in methanol:acetone. Fixed cells were incubated overnight at 5° C. with mouse sera (1:200/1:400/1:800) or monoclonal antibodies, followed by incubation for 45 min at room temperature with FITC-conjugated rabbit anti-mouse immunoglobulins (Dako, Denmark). Slides were mounted in glycerol containing p-phenylenediamine and examined in a Zeiss fluorescence microscope.

Immunohistochemistry

Frozen tissue samples were fixed for 10 min in cold methanol/acetone (50:50). Formalin fixed, paraffin wax embedded tissues of breast carcinoma were obtained from files of Institute of Molecular Pathology and Immunology of the University of Porto, Portugal. All cases were conventionally classified by histological type. The avidin-biotin-peroxidase complex method was used for immunostaining. Paraffin sections were dewaxed, rehydrated, and treated with 0.5% $H_2O_2$ in methanol for 30 min. Section were rinsed in TBS and incubated for 20 min with rabbit nonimmune serum. Sections were rinsed and incubated overnight at 5° C. with primary antibody. Sections were rinsed and incubated with biotin-labeled rabbit anti-mouse serum (Dako, Denmark) diluted 1:200 in TBS doe 30 min, rinsed with TBS, and incubated for 1 h with avidin-biotin-peroxidase complex (Dako, Denmark). Sections were rinsed with TBS and developed with 0.05% 3,3'-diaminobenzidine tetrahydrochloride freshly prepared in 0.05 M TBS containing 0.1% $H_2O_2$. Sections were stained with hematoxylin, dehydrated and mounted.

Results

Chemoenzymatic Synthesis of Multimeric Tn and STn MUC1 Glycopeptides.

Synthetic 60-mer MUC1 tandem repeat peptides were glycosylated using site-selective recombinant polypeptide GalNAc-transferases (GalNAc-T2, -T4 and -T11). The sites of GalNAc attachments in MUC1 tandem repeat sequences were strictly controlled as indicated by MALDI-TOF mass spectrometry analysis of MUC1 60-mer tandem repeat peptides glycosylated in vitro with recombinant GalNAc-transferases. GalNAc-T11 was used to add 2 GalNAc residues per tandem repeat, GalNAc-T2 to add 3 residues, and sequential use of GalNAc-T2 and -T4 to add all 5 residues (FIG. 1). Sites of attachments were confirmed by mass spectrometry as previously described. Glycosylation with GalNAc-T4 to achieve five GalNAc residues per repeat only allowed 14 in total due to the design of the peptide with the $NH_2$-terminal being too truncated. Further glycosylation of GalNAc residues with sialic acid to form STn was achieved with recombinant murine ST6GalNAc-I. Evaluation of number of sialic acid residues attached by MALDI-TOF may be underestimated due to the labile nature of this sugar linkage. The sialylation is considered complete as evaluated by immunoreactivity pattern with anti-STn (positive) and anti-Tn (negative) monoclonal antibodies. The core 1 T structure was produced using a recombinant β3Gal-transferase. Glycopeptides formed are depicted on top of each MALDI-TOF profile in FIG. 1.

MUC1 Glycopeptides with Complete O-Glycan Attachment are Most Immunogenic and Tn and STn Glycopeptides Elicit Strong Antibody Responses in MUC1 Transgenic Mice.

In initial studies MUC1 Tn glycoforms with 2, 3 and 5 O-glycans per repeat were tested as immunogens, and the glycopeptide with 3 and 5 O-glycans yielded the strongest immune response to the respective immunogens by ELISA and more importantly induced antibodies reactive with MUC1 expressing cancer cells (not shown). For the further studies MUC1 with complete O-glycan occupancy was chosen, and as shown in FIG. 2 sera from wild-type Balb/c mice (FIG. 2ac) and MUC1.Tg mice (FIG. 2bd) immunized with either the complete Tn glycosylated MUC1 ($MUC1_{60}Tn_{15}$) or the complete STn glycosylated MUC1 glycopeptide ($MUC1_{60}STn_{15}$) yielded high antibody titers in both mice. The highest antibody titers were found with the MUC1 glycoform used as immunogen, but considerable reactivity with the other MUC1 glycoforms were found as well. Low reactivity with unglycosylated MUC1 was found particularly in the Tn immunized mice. Very low levels of anti-Tn and STn hapten antibodies were detected using the mucin OSM (ovine submaxillary mucin with mainly STn glycoform) and A-OSM (asialo-mucin with Tn glycoform) as antigens. No reactivity with non-MUC1 peptides or glycopeptides with Tn-glycosylation were found.

Characterization of a Monoclonal Antibody 5E5 That Mimics the Immune Response Elicited in Wild Type and MUC1.Tg Mice Immunized with Tn MUC1.

In order to further characterize and define the specificity of the immune response to the glycopeptides, we isolated a monoclonal antibody (designated 5E5) from a mouse immunized with the complete Tn glycosylated MUC1 glycopeptide, which essentially mirrored the specificity of the polyclonal response found (FIG. 3a). The antibody 5E5 reacted with all Tn and STn glycoforms of the MUC1 tandem repeat and showed no reactivity with unglycosylated MUC1 peptides and only very weak reactivity with the Tn hapten presented on non-MUC1 peptide backbone. In order to evaluate the range of O-glycan structures involved in the specificity we took advantage of the CHO ldlD cell system. CHO ldlD cells lack the UDP-Gal/GalNAc epimerase and are deficient in GalNAc O-glycosylation and galactosylation in the absence of exogenous addition of GalNAc and Gal, respectively. CHO ldlD cells stably transfected with the full coding human MUC1 gene (CHO ldlD/MUC1) were grown in the presence of GalNAc, in the presence of Gal and GalNAc or in the absence of both, yielding cells expressing Tn, ST, or unglycosylated MUC1 glycoforms, respectively. As shown in FIG. 3b the CHO ldlD MUC1 cells express MUC1 as detected by the general anti-MUC1 antibody HMFG2 regardless of addition of sugars to the growth medium. Cells grown in GalNAc alone express as expected only Tn antigen and not T or ST, while cells grown in Gal and GalNAc as expected only express ST. Interestingly, cells grown in GalNAc alone do not express the STn structure, which indicate that the CHO ldlD cells do not express significant amounts ST6GalNAc-I. The staining of the anti-carbohydrate antibodies was highly dependent on expression of MUC1 since non-transfected CHO ldlD cells only showed very weak reactivity (not shown). Further confirmation of the MUC1 glycoforms produced by CHO ldlD cells have been achieved by mass spectrometric analysis of a secreted MUC1-IgG chimeric construct grown with or without sugars (results to be published elsewhere). 5E5 specifically reacted with the Tn glycoform of recombinant MUC1 expressed in the CHO ldlD cells and did not react with unglycosylated or further glycosylated T and ST MUC1 glycoforms (FIG. 3*bc*). 5E5 defined a cancer-associated glycoform of MUC1 strongly expressed in most breast cancers (Table I, FIG. 3*d*). 5E5 stained all ductal carcinomas (n=18) and 2 lobular carcinomas. The percentage of positive cells varied among less than 25% to more than 75%. 6 cases of benign lesions were stained, of these only 2 (1 fibrosis and 1 fibroadenoma) showed positive staining with 5E5 and in these cases less than 25% of the cells stained. This staining pattern closely followed that of monoclonal antibody HMFG2 in cancer, but 5E5 was more restricted in normal breast and benign lesions. This further indicates that Tn and STn MUC1 tandem repeat glycopeptides represent prime vaccine candidates.

TABLE I

Immunochemical staining of human breast tissue with anti-MUC1 monoclonal antibodies

| | | | | 5E5 | | HMFG2 | |
|---|---|---|---|---|---|---|---|
| Tissue sample | Pathology | Grade | Node | Proportion of tumor cells stained | Intensity | Proportion of tumor cells stained | Intensity |
| 1014 (B) 1 | Normal | | | − | − | + | + |
| 1020 (A2) | Normal | | | − | − | − | − |
| 1073 (A) | Normal | | | − | − | − | − |
| 1168 (B) | Normal | | | − | − | + | ++ |
| 1196 (A) | Normal | | | − | − | + | ++ |
| 1076 (B) | Normal | | | − | − | − | − |
| 950 (B) | Normal | | | − | − | − | − |
| 91 (K) | Duct hyperplasia | | | − | − | + | ++ |
| 585 (A) | Duct hyperplasia | | | − | − | − | − |
| 364 (B) | Fibrocystic, duct hyperplasia | | | − | − | <25% | ++ |
| 60 (B) | Fibrocystic, duct hyperplasia | | | − | − | <25% | + |
| 35 (B) | Fibrosis | | | <25% | +++ | <25% | ++ |
| 1309 (B) | Fibroadenoma | | | <25% | +++ | <25% | +++ |
| 268H | Lobular carcinoma | | − | 50-75% | ++ | 50-75% | +++ |
| 83 | Lobular carcinoma | | + | 25-50% | +++ | ND | ND |
| 508 K III | Ductal carcinoma | II | − | 50-75% | +++ | 50-75% | +++ |
| 314 G | Ductal carcinoma | II | − | 25-50% | +++ | 25-50% | +++ |
| 558 F | Ductal carcinoma | II | − | 50-75% | +++ | 50-75% | +++ |
| 658 M | Ductal carcinoma | II | + | 50-75% | +++ | <25% | + |
| 58 DI | Ductal carcinoma | III | − | 25-50% | +++ | 25-50% | +++ |
| 390 L | Ductal carcinoma | III | − | <25% | +++ | <25% | +++ |
| 726 H III | Ductal carcinoma | III | − | >75% | +++ | >75% | +++ |
| 393 A | Ductal carcinoma | III | + | <25% | +++ | 25-50% | +++ |
| 418 J II | Ductal carcinoma | III | + | 50-75% | +++ | 50-75% | +++ |
| 341 | Ductal carcinoma | III | + | 50-75% | +++ | ND | ND |
| 456 | Ductal carcinoma | III | + | >75% | +++ | ND | ND |
| 57 | Ductal carcinoma | I | − | 50-75% | +++ | ND | ND |
| 182 | Ductal carcinoma | I | − | 25-50% | +++ | ND | ND |
| 313 E | Ductal carcinoma | I | + | 25-50% | +++ | ND | ND |
| 579 | Ductal carcinoma | I | + | 25-50% | +++ | ND | ND |
| 1185 | Ductal carcinoma | I | + | <25% | +++ | ND | ND |

TABLE I-continued

Immunochemical staining of human breast tissue with anti-MUC1 monoclonal antibodies

| Tissue sample | Pathology | Grade | Node | 5E5 Proportion of tumor cells stained | 5E5 Intensity | HMFG2 Proportion of tumor cells stained | HMFG2 Intensity |
|---|---|---|---|---|---|---|---|
| 207 | Ductal carcinoma | I | + | 50-75% | +++ | ND | ND |
| 899 | Ductal carcinoma | I | + | – | – | ND | ND |

Intensity:
−: no staining;
+: weakly positive;
++: moderately positive;
+++: strongly positive
ND: not determined MUC1.Tg Mice Immunized with Tn and STn MUC1 Glycopeptides Produce MUC1 Glycopeptide Specific Responses Restricted to Cancer-Associated MUC1 Glycoforms.

MUC1 tandem repeat peptide vaccines have generally been ineffective in inducing humoral responses to the cancer associated MUC1, when the mucin is expressed as a self antigen, presumably due to tolerance. However, as shown in FIG. 2 both the Tn and STn 60-mer MUC1 glycopeptides induced strong antibody responses to the glycopeptides in MUC1 transgenic mice. The specificities of the antibody responses were essentially identical to those found in wild type mice. The Ig subclass distribution was primarily of IgG1, but responses to STn 60-mer MUC1 included IgG2A and IgG2B subclasses indicating significant class switching (not shown). The elicited antibodies reacted with recombinant Tn MUC1 expressed in CHO ldlD cells (FIG. 4a) similar to wild type sera (not shown) and the monoclonal antibody 5E5 (FIG. 3b). Furthermore, sera from mice immunized with Tn MUC1 glycopeptides reacted strongly with the human breast cancer cell line T47D, which mainly carry Tn but also some T and ST O-glycans. Sera raised against MUC1$_{60}$Tn$_{15}$ showed strong staining of T47D cells. Sera from mice immunized with MUC1 60-mer carrying 2 or 3 Tn per tandem repeat sequence showed intermediate levels of reactivity with the tumor cell line. Sera from MUC1.Tg mice immunized with MUC1$_{60}$Tn$_{15}$ showed intermediate staining of T47D. Another breast cancer cell line, MCF7, has been shown to express MUC1 with O-glycans partially based on core 2 structures and thus has a glycosylation pattern that more closely resembles the pattern found in normal epithelial cells. Sera from mice immunized with MUC1$_{60}$Tn$_{15}$ showed lower reactivity with MCF7 than with T47D cells. MCF7 was not stained by sera raised against MUC1$_{60}$STn$_{15}$. All sera demonstrated very low reactivity with the non-tumorigenic epithelial cell line MTSV1-7, which expresses high levels of C2GnT1 and produces MUC1 carrying core 2 based O-glycans. Finally, anti-sera from the MUC1 transgenic mice immunized with MUC1$_{60}$STn$_{15}$ reacted with primary breast carcinomas expressing MUC1 and STn (FIG. 4b).

Example 2

Materials and Methods
Chemoenzymatic Synthesis of Glycopeptides

A MUC1 60-mer peptide (VTSAPDTRPAPGSTAP-PAHG)$_{n=3}$ (SEQ ID NO. 1) representing three tandem repeats was synthesized (by Cancer Research UK) as originally reported. For immunization of mice, the peptide was completely Tn-glycosylated in vitro by concerted action of GalNAc-T2 and -T4 (see below). For capture ELISA, an NH$_2$-terminal biotinylated variant of the 60-mer peptide was in vitro glycosylated to form 11 different glycoforms (FIG. 5). Furthermore, as control peptide a MUC2 33-mer peptide (PTTTPITTTTTVTPTPTPTGTQTPTTTPISTTC) (SEQ ID NO. 14) corresponding to 1.4 tandem repeat (kindly provided by Dr. P. O. Livingston) was Tn-glycosylated by GalNAc-T2 with an occupancy of approximately 12 out of 20 potential acceptor sites. Two valine-substituted NH$_2$-terminal biotinylated 25-mer MUC1 peptides, TAP25V9 (T$^1$APPAHGVV$^9$SAPDTRPAPGST$^{21}$APPA) (SEQ ID NO. 10) and TAP25V21 (T$^1$APPAHGVT$^9$SAPDTRPAPGSV$^{21}$APPA), (SEQ ID NO. 11) were synthesized and their glycosylation products with different polypeptide GalNAc-transferases characterized as previously described. These peptides were enzymatically in vitro glycosylated at Thr$^1$ and Thr$^{21}$ or Thr$^1$ and Thr$^9$, respectively, by using GalNAc-T11 (FIG. 5). Furthermore, eight different 21-mer MUC1 glycopeptides with either a single Tn-glycan (Tn-A1-Tn-A4) or a single T-glycan (T-A1-T-A4) based on the sequence AHGVTSAPDTRPAPG-STAPPA (SEQ ID NO. 12) were chemically synthesized (FIG. 5).

Conjugation of MUC1 60-Mer Glycopeptide for Immunization 60-mer MUC1 peptide carrying 15 GalNAc residues was conjugated to Imject® Mariculture Keyhole Limpet Hemocyanin (mcKLH) (Pierce Biotechnology, Inc., Rockford, Ill.) using glutaraldehyde in a molar ratio of glycopeptide:mcKLH 300:1. Excess glutaraldehyde was removed on PD-10 desalting columns (Amersham Biosciences, Uppsala, Sweden) eluting in PBS. Fractions were pooled based on OD readings at 280 nm and 210 nm. The fractions corresponding to the elution time of the unconjugated peptides did not contain peptide according to OD reading at 210 nm. Furthermore, in ELISA, the rate of conjugation was estimated to be nearly complete by comparing reactivity of the conjugates and the corresponding unconjugated glycopeptides with monoclonal antibodies directed to the glycopeptide or the glycan alone.

Production of Recombinant MUC1 in CHO ldlD Cells

CHO ldlD cells stably transfected with a soluble MUC1-murine IgG2a fusion construct containing 16 tandem repeats were cultured in Iscove's modified Dulbecco's medium with 10% FCS and 600 µg/ml G418. Exploiting the deficiency of UDP-Gal/UDP-GalNAc 4-epimerase in these cells, culturing with 1 mM GalNAc yielded cells expressing soluble Tn-MUC1, whereas culturing with 1 mM GalNAc and 0.1 mM Gal yielded cells expressing soluble ST-MUC1. Glycoproteins (6×His-tagged) were purified on Ni-NTA agarose (Qiagen, Hilden, Germany). Purified ST-MUC1 was treated with neuraminidase (0.2 U/ml in 50 mM sodium acetate buffer, pH 5.5) to render T-MUC1 followed by re-purification on Ni-NTA agarose for removal of neuraminidase.

Generation of MAb 2D9

Similarly to MAb 5E5, female Balb/c mice were immunized with 15Tn-MUC1 60-mer glycopeptide conjugated to KLH. Tail bleeds were collected seven days after the third immunization and sera tested by ELISA with the Tn-MUC2 glycopeptide serving as negative control, or by immunocytochemistry with CHO ldlD MUC1F cells expressing Tn-MUC1, ST-MUC1 (T-MUC1 after neuraminidase treatment) or unglycosylated MUC1, T47D (human ductal breast carcinoma), MCF7 (human breast carcinoma), and MTSV1-7 (human breast). Three days after the fourth immunization, spleen cells from one mouse were fused with NS1 myeloma cells. Hybridomas specific to the antigens of interest were cloned by limiting dilution at least three times.

Other Monoclonal Antibodies

Two control antibodies were raised in female Balb/c mice against purified soluble MUC1 from CHO ldlD MUC1 cells grown in GalNAc (MAb 5E10) or Gal and GalNAc, followed by neuraminidase treatment (MAb 1B9). Immunizations were performed by one subcutaneous injection of 40 µg/100 µl of immunogen emulsified in Freund's complete adjuvant followed by two injections with Freund's incomplete adjuvant at 2-3 weeks intervals and finally a boost without adjuvant. The two clones were selected by immunocytochemistry as described above with different selection criteria. MAb 5E10 was selected since it reacted with all the tested MUC1 expressing cell lines independently of O-glycosylation and therefore potentially could serve as a universal anti-MUC1 MAb. MAb 1B9 was selected because it showed specificity for neuraminidase treated cells presenting the T antigen.

ELISA-Assays

Enzyme-linked immunosorbent assays (ELISA) were performed using Nunc-Immuno MaxiSorp F96 plates (Nunc, Roskilde, Denmark). Unbiotinylated glycopeptides were serially diluted from an initial concentration of 2 µg/ml and coated 1 h at 37° C. or over night at 4° C. in carbonate-bicarbonate buffer (pH 9.6). For capture ELISA, plates were coated 1 h at 37° C. or over night at 4° C. with 1.5 µg/ml of streptavidin (Sigma-Aldrich, St. Louis, Mo.) in carbonate-bicarbonate buffer (pH 9.6). Plates were blocked with Super-Block Blocking Buffer (Pierce, Rockford, Ill.) for 1 h at room temperature. The streptavidin-coated plates were incubated with biotinylated glycopeptides serially diluted from an initial concentration of 2 µg/ml and incubated for 1 h at 37° C. or over night at 4° C. Subsequently, plates were incubated with monoclonal antibodies for 2 h at room temperature or over night at 4° C. 5E5, 2D9, 1B9, 5E10, and SM3 were used as undiluted culture supernatants, whereas MY.1E12 ascites were used 1:1000 and purified BW835 was used at 1 µg/ml. MY.1E12 was kindly provided by Dr. T. Irimura, and BW835 by Drs. F. -G. Hanisch and T. Schwientek. Sera from MUC1 transgenic mice immunized with Tn-MUC1 were serially diluted in 2% BSA in PBS from an initial dilution of 1:100 or 1:200. Bound antibodies were detected with HRP-conjugated polyclonal rabbit anti-mouse immunoglobulins (Dako, Glostrup, Denmark). Plates were developed with TMB+ one-step substrate system (Dako, Glostrup, Denmark), reactions stopped with 1 N $H_2SO_4$, and read at 450 nm.

Immunocytochemistry

Cell lines were fixed for 10 min in ice-cold acetone. Fixed cells were incubated overnight at 4° C. with undiluted MAb supernatants, followed by incubation for 45 min at room temperature with fluorescein isothiocyanate (FITC)-conjugated rabbit anti-mouse immunoglobulins (Dako, Glostrup, Denmark). Slides were mounted in glycerol containing p-phenylenediamine and examined in a Zeiss fluorescence microscope (FluoresScience, Hallbergmoos, Germany).

Results

Generation of MUC1 Monoclonal Antibodies

The MAb 5E5 (IgG1) was raised against 60-mer MUC1 tandem repeat peptide carrying 15 GalNAc residues conjugated to KLH as described previously (Sorensen et al. 2006). This antibody was shown to specifically react with MUC1 carrying Tn or STn in the tandem repeat domain and reacts with the vast majority of breast carcinomas while showing no reactivity with normal breast epithelia (Sorensen et al. 2006). 5E5 was originally selected because its reactivity pattern essentially mirrored that of total sera from MUC1 transgenic mice immunized with MUC1 tandem repeat glycopeptides with complete Tn- or STn-glycosylation (Sorensen et al. 2006). In the present study, we have reproduced the immunization and screening protocol and isolated another monoclonal antibody, 2D9 (IgG1), which exhibits essentially the same specificity (FIG. 6), demonstrating that such antibodies are prevalent.

Two additional MUC1 antibodies were raised against purified recombinant secreted MUC1 (rMUC1) expressed in CHO ldlD cells grown in GalNAc to produce the Tn glycoform (5E10) or grown in Gal and GalNAc to produce the ST glycoform, which after neuraminidase treatment was reduced to the T glycoform (1B9). By immunocytochemistry, MAb 5E10 reacted with all the MUC1 expressing cell lines tested and therefore potentially could serve as a universal anti-MUC1 MAb. MAb 1B9 was selected because it showed specificity for neuraminidase treated cells presenting the T glycoform of MUC1 (data not shown).

Epitope Mapping of MAbs 5E5 and 2D9 Raised Against Tn-MUC1 Tandem Repeat Glycopeptides The specificity of the antibodies was initially determined by direct binding ELISA assays using a panel of 60-mer glycopeptides produced by chemoenzymatic methods (FIG. 5) (Sorensen et al. 2006). The MAbs 5E5 and 2D9 exhibited a similar reactivity pattern with high selectivity for MUC1 tandem repeat glycopeptides with Tn and STn O-glycans and both antibodies showed preference for Tn-MUC1 glycoforms with highest O-glycan occupancy; however, in direct binding assays, 2D9 showed significantly better reactivity with Tn glycoforms compared to STn glycoforms (not shown). In order to fully assess the binding specificity of the antibodies and eliminate issues with differences in adsorption and presentation of MUC1 peptides and glycopeptides in direct binding ELISA assays, a streptavidin-biotin capture ELISA was developed using a large panel of 60-mer based MUC1 biotinylated glycopeptides (FIG. 5). The results shown in FIG. 6 clearly confirm that the two MAbs, 5E5 and 2D9, react with a glycopeptide epitope where the glycan can be Tn or STn, with at least two O-glycans and preferably three or five O-glycans per MUC1 repeat. This could suggest that an O-glycan in either the VTSA (SEQ ID NO. 6) or the GSTV (SEQ ID NO. 13) region of the sequence is required for the epitope (FIG. 5). Recombinant expression of MUC1 in CHO ldlD cells allows presentation of different glycoforms of MUC1 (Sorensen et al. 2006). MAbs 5E5 and 2D9 reacted with Tn-MUC1 but not with T-MUC1 glycoforms as predicted by the lack of reactivity with T and ST-MUC1 glycopeptides (FIG. 6, panels A and D). Interestingly, weak reactivity was observed with the core 3 O-glycosylated glycoform (GlcNAcβ1-3GalNAcα1-O-Ser/Thr) but only when this is presented with three and not with five O-glycans per tandem repeat. The significance of this is not clear at present, and expression of the β3Gn-T6 enzyme synthesizing the core 3 O-glycan structure is limited to stomach, colon, and small intestine.

Further glycopeptide variants are required to more precisely define the epitopes; however, present enzymatic glycosylation of 60-mer MUC1 peptides are limited by the substrate specificities of polypeptide GalNAc-transferases. Therefore, two 25-mer peptides with valine substitutions of selected threonine residues were used to chemoenzymatically produce glycoforms with Tn at individual sites utilizing GalNAc-T11 (FIG. 5). Besides Tn-glycosylation of the initial Thr, the two glycopeptides were either Tn-glycosylated at Thr in the VTSA (SEQ ID NO. 6) region (2Tn-TAP25V21) or at Thr in the GSTA (SEQ ID NO. 7) region (2Tn-TAP25V9). Enzymatic Tn-glycosylation of both Ser and Thr in the GSTA (SEQ ID NO. 7) region, which was observed to increase reactivity with the biotinylated 60-mer peptide, was not possible with the TAP25V9 peptide. As shown in FIG. 6 (Panels B and E) 5E5 and 2D9 did not react with 2Tn-TAP25V21 with Tn-glycosylation at Thr in the VTSA (SEQ ID NO. 6) region, whereas strong reactivity was found with the 2Tn-TAP25V9 glycopeptide with Tn-glycosylation at Thr in the GSTA (SEQ ID NO. 7) region. This reactivity pattern was confirmed in direct binding ELISA with a panel of synthetic MUC1 glycopeptides with one single Tn or T O-glycan (FIG. 5). 5E5 and 2D9 showed strong reactivity towards the glycopeptide with Tn at the Thr in the GSTA (SEQ ID NO. 7) region, whereas no reactivity was seen when the T glycan was carried on this threonine or with the other Tn- or T-glycosylated glycopeptides (FIG. 6, panels C and F). In summary, 5E5 and 2D9 reacted with MUC1 glycopeptides when Thr in GSTA (SEQ ID NO. 7) is Tn- or STn-glycosylated and stronger when both Ser and Thr are glycosylated.

Specificity Analysis of Total Serum from Tn-MUC1 Immunized MUC1 Transgenic Mice

Total serum of mice immunized with the 15Tn-MUC1 60-mer glycopeptide conjugated to KLH showed the same preference for high-density Tn- and STn-MUC1 glycopeptides (FIG. 7, panel A). More importantly, the same specificity for the Tn-glycosylated GSTA (SEQ ID NO. 7) sequence was observed with the valine-substituted glycopeptides (FIG. 7, panel B). Taken together with the data above, these results clearly indicate that the GSTA (SEQ ID NO. 7) region of the MUC1 tandem repeat glycosylated with Tn and/or STn represents a novel immunodominant MUC1 glycopeptide epitope.

Characterization of MAbs 1B9 and 5E10

The two MAbs raised against recombinant MUC1 glycoprotein expressed in CHO ldlD cells were analyzed with the capture ELISA using the panel of MUC1 60-mer biotinylated glycopeptides. MAb 1B9 showed strong reactivity with the MUC1 glycopeptide with three T O-glycans per tandem repeat, whereas only an extremely weak reaction was observed with the glycopeptide fully substituted with five T O-glycans per tandem repeat (FIG. 8, panel A). Intermediate reactivity was seen with peptides substituted with core 3 and ST, but only with peptides with three glycans per tandem repeat (FIG. 8, panel A). ELISA with MUC1 glycopeptides with one single T O-glycan showed reactivity with the peptide T-glycosylated at Thr in the amino acid sequence GSTA (SEQ ID NO. 7), but also, although weaker, with the peptide T-glycosylated at Thr in the amino acid sequence VTSA (SEQ ID NO. 6) (FIG. 8, panel B). No reactivity was seen with the MUC1 glycopeptides with one single Tn O-glycan. Furthermore, 1B9 did not react with CHO ldlD MUC1-expressing cells when grown in GalNAc alone, but only when Gal is added to the growth medium, leading to expression of ST-MUC1. Significantly enhanced reactivity was seen after neuraminidase treatment of the cells to expose T-MUC1 (FIG. 8, panel C). These data suggest that the epitope for 1B9 is not a glycopeptide epitope, but rather a conformational epitope requiring glycosylation with β1-3 linked disaccharides (T or core 3) in either the VTSA (SEQ ID NO. 6) or the GSTA (SEQ ID NO. 7) regions, but not the PDTR (SEQ ID NO. 4) region.

The MAb 5E10 showed highest reactivity with biotinylated MUC1 60-mer peptide or when the peptide is either unglycosylated or substituted with only two Tn glycans per tandem repeat. Reactivity towards Tn-glycosylation decreased with increasing density of glycosylation. An additional decrease in reactivity was seen with the introduction of T-glycosylation, followed by a further decrease by introduction of core 3 glycosylation. Lowest reactivity was seen with increasing degrees of sialylation, especially when NeuAc is α2-6-linked to GalNAc (STn). No reactivity at all was seen with the peptide fully substituted with STn (FIG. 9, panel A). In ELISA with biotinylated valine-substituted in vitro Tn-glycosylated MUC1 peptides, equal reactivity was seen with all four peptides regardless of glycosylation (FIG. 9, panel B). In ELISA with MUC1 glycopeptides with one single Tn or T O-glycan, equal reactivity was seen with all peptides except for the peptide T-glycosylated at Thr in the amino acid sequence GSTA (SEQ ID NO. 7) (FIG. 9, panel C). In immunocytology, 5E10 reacted with CHO ldlD MUC1-expressing cells independently on co-culturing with GalNAc, Gal, or no sugar at all (data not shown). In summary, 5E10 reacted with all MUC1 glycoforms tested with the exception of complete STn occupancy.

Comparison with Other MAbs Previously Reported to React with MUC1 Glycoforms

The MAb SM3 binds the PDTR region of the MUC1 tandem repeat and Tn-glycosylation of the Thr enhances its binding. In agreement with previous reports, SM3 preferentially reacted with unglycosylated peptide and the glycopeptides with complete O-glycan occupancy of five O-glycans per tandem repeat, while reactivity with glycopeptides with two and three O-glycans was lower (FIG. 9, panel D). These results confirm and extend our previous studies to demonstrate that T, ST and core 3 O-glycans react equally well. For this study we did not have core 2 glycoforms, but studies with cell lines clearly indicate that core 2 glycosylation of MUC1 blocks the SM3 epitope. Little reactivity was observed with the biotinylated valine-substituted peptides, whether unglycosylated or with Tn-glycosylation of Thr in the amino acid sequences VTSA (SEQ ID NO. 6) or GSTA (SEQ ID NO. 7) (FIG. 9, panel E). In ELISA with MUC1 glycopeptides with one single Tn or T O-glycan, high reactivity was seen when Thr in the amino acid sequence PDTR (SEQ ID NO. 4) is substituted with either T or Tn. Lower reactivity was seen with the remaining T-MUC1 glycopeptides, whereas hardly any reactivity was observed with the remaining Tn-MUC1 glycopeptides (FIG. 9, panel F).

MAb BW835 reacted in the capture ELISA with biotinylated MUC1 60-mer glycopeptides fully glycosylated with the disaccharides T (FIG. 8, panel C). Interestingly, BW835 reacted equally well with the core 3 O-glycosylated peptide indicating that the antibody does not require the T glycoform per se. Lower reactivity was also found with the fully ST-glycosylated peptide. Weak reactivity was observed with the T glycopeptide with only three O-glycans, and similar weak reactivity was found with the fully Tn-glycosylated glycopeptide. No reactivity was found with glycopeptides carrying two or three Tn glycans per TR, STn-glycosylated, or unglycosylated peptides. These results are in agreement with and extend previous characterization of the epitope.

In accordance with earlier published data, MY.1E12 showed strict specificity for the ST-glycoforms of MUC1 as evaluated with biotinylated 60-mer glycopeptides (FIG. 8, panel D). In contrast to BW835, MY.1E12 showed preference for the peptide with three ST O-glycans per tandem repeat, suggesting that the epitope is at least partially destroyed when both Thr and Ser in the VTSA (SEQ ID NO:6) region are glycosylated.

Example 3

Materials and Methods

A MUC1 60-mer peptide (VTSAPDTRPAPGSTAP-PAHG)$_{n=3}$ (SEQ ID NO. 1) representing three tandem repeats is glycosylated in vitro with 5 moles of Tn, STn, and T as described in Examples 1 and 2. Control glycopeptides includes the MUC2 33-mer peptide (PTTTPIT-TTTTVTPTPTPTGTQTPTTTPISTTC) (SEQ ID NO. 14) with the same glycoforms. Murine monoclonal anti-MUC1 antibodies, 5E10, 5E5 and 1B9, were described in Example 2. Murine monoclonal antibodies to Tn (3E1, 5F4), T (3F1, TKH2) and T (HHB, 3C9) are produced as previously described (Kjeldsen et al, 1989; Kjeldsen et al, 1988; Hirohashi et al, 1985; Clausen et al, 1988). Monosaccharides GalNAc, GlcNAc, Gal, Glc and NeuAc are bought from Sigma, GalNAcα-agarose (GlycoSorb-1) is bought from GlycoRex. OSM and asialo-OSM are prepared as previously described (Reis et al, 1998b; Reis et al, 1998a). BSM is bought from Sigma and asialo-BSM prepared as previously described by neuraminidase treatment (Reis et al, 1998b; Reis et al, 1998a). Tn (GalNAcα1-), STn (NeuAcα2-6GalNAcα1-) and T (Galβ1-3GalNAcα1-) polyvalent PAA conjugates are bought from GlycoTech.

ELISA-Assays

Enzyme-linked immunosorbent assays (ELISA) are performed using Nunc-Immuno MaxiSorp F96 plates (Nunc, Roskilde, Denmark). Peptides and glycopeptides are coated at concentrations of 1, 0.2, and 0.05 µg/ml for 1 h at 37° C. or over night at 4° C. in carbonate-bicarbonate buffer (pH 9.6). Plates are blocked with SuperBlock Blocking Buffer (Pierce, Rockford, Ill.) for 1 h at room temperature. Subsequently, plates are incubated with dilutions of monoclonal anti-MUC1 antibodies 5E5, 1B9, and 5E10 and anti-carbohydrate antibodies 3E1, 5F4, 3F1, TKH2, HHB, and 3C9 (starting from undiluted culture supernatants) for 2 h at room temperature. In subsequent inhibition experiments fixed concentrations of (glyco)peptides and monoclonal antibodies are used, and the appropriate dilution of monoclonal antibodies are preincubated with serially diluted inhibitor carbohydrates and glycoconjugates (starting from 0.5M for monosaccharides, 10 µg/ml (glyco)peptides, 100 µg/ml for PAA conjugates and 10 µg/ml mucins) for 30 min at room temperature, before transfer to coated ELISA plates. Bound antibodies are detected with HRP-conjugated polyclonal rabbit anti-mouse immunoglobulins (Dako, Glostrup, Denmark). Plates are developed with TMB+ one-step substrate system (Dako, Glostrup, Denmark), reactions stopped with 1 N H2504, and read at 450 nm.

Results

Determination of End-Point Titer of Antibodies

Initial ELISA assays are performed to define appropriate coating concentrations of peptides and glycopeptides and appropriate dilutions of antibodies for further inhibition assays. For each antibody appropriate antigen and antibody dilutions are determined by evaluation of end-point titer and conditions yielding OD450 readings of approximately 1 are used for further studies.

Inhibition of antibody binding to glycopeptides with Tn, STn and T glycosylation—Antibodies to carbohydrate haptens—The antibodies reactive with Tn, STn and T irrespective of the peptide backbone of glycopeptides reacts with both MUC1 and MUC2 glycopeptides with the respective glycoforms.

Thus, anti-Tn antibodies 1E3 and 5F4 reacts only with the Tn-glycopeptides, anti-STn antibodies TKH2 and 3F1 reacts only with the STn-glycopeptides, while anti-T antibodies react with T-glycopeptides. Inhibition ELISA assays further demonstrate that binding to the respective glycopeptides can be inhibited by the corresponding glycopeptides, mucins (Tn antibodies with asialo-OSM, STn antibodies with OSM and T antibodies with asialo-BSM, PAA conjugates, as well as with high concentrations of monosaccharides (Tn antibodies with GalNAc, STn antibodies with NeuAc, and T antibodies with Gal). Furthermore, the GlycoSorb-1 Tn adsorbant can inhibit the Tn antibodies.

Antibodies to MUC1—The antibody reactive with the MUC1 peptide (5E10) is inhibited by all MUC1 peptides and glycopeptides, whereas MUC2 peptides and glycopeptides as well as all other glycans and glycoconjugates can not inhibit. In striking contrast, the MUC1 Tn/STn glycoform specific antibodies 5E5 and 2D9 are inhibited only by Tn-MUC1 glycopeptides and to a much lesser degree by STn-MUC1 glycopeptides. Similarly, the MUC1 T glycoform specific antibody 1B9 is only inhibited by the T-MUC1 glycopeptides.

REFERENCES

Burchell, J. M., Mungul, A. & Taylor-Papadimitriou, J. (2001). O-linked glycosylation in the mammary gland: changes that occur during malignancy. *J. Mammary. Gland. Biol. Neoplasia.*, 6, 355-364.

Clausen, H., Stroud, M., Parker, J., Springer, G., & Hakomori, S. (1988) Monoclonal-Antibodies Directed to the Blood Group-A Associated Structure, Galactosyl-A-Specificity and Relation to the Thomsen-Friedenreich Antigen. *Molecular Immunology*, 25, 199-204.

Hanisch, F. G., Stadie, T. & Bosslet, K. (1995). Monoclonal antibody BW835 defines a site-specific Thomsen-Friedenreich disaccharide linked to threonine within the VTSA motif of MUC1 tandem repeats. *Cancer Res.*, 55, 4036-4040.

Kjeldsen, T., Clausen, H., Hirohashi, S., Ogawa, T., Iijima, H., & Hakomori, S. (1988) Preparation and Characterization of Monoclonal-Antibodies Directed to the Tumor- Associated O-Linked Sialosyl-2-]6 Alpha-N-Acetylgalactosaminyl (Sialosyl-Tn) Epitope. *Cancer Research*, 48, 2214-2220.

Kjeldsen, T., Hakomori, S., Springer, G. F., Desai, P., Harris, T., & Clausen, H. (1989) Coexpression of Sialosyl-Tn (Neuac-Alpha-2-]6Galnac-Alpha-1-]O-Ser/Thr) and Tn (Galnac-Alpha-1-]O-Ser/Thr) Blood-Group Antigens on Tn Erythrocytes. *Vox Sanguinis*, 57, 81-87.

Mensdorff-Pouilly, S., Petrakou, E., Kenemans, P., van Uffelen, K., Verstraeten, A. A., Snijdewint, F. G. M., van Kamp, G. J., Schol, D. J., Reis, C. A., Price, M. R., Livingston, P. O., & Hilgers, J. (2000) Reactivity of natural and induced human antibodies to MUC1 mucin with MUC1 peptides and N-acetylgalactosamine (GalNAc) peptides. *International Journal of Cancer*, 86, 702-712.

Reis, C. A., Hassan, H., Bennett, E. P., & Clausen, H. (1998a) Characterization of a panel of monoclonal antibodies using GalNAc glycosylated peptides and recombinant MUC1. *Tumor Biology*, 19, 127-133.

Reis, C. A., Sorensen, T., Mandel, U., David, L., Mirgorodskaya, E., Roepstorff, P., Kihlberg, J., Hansen, J. E. S., & Clausen, H. (1998b) Development and characterization of an antibody directed to an alpha-N-acetyl-D-galactosamine glycosylated MUC2 peptide. *Glycoconjugate Journal*, 15, 51-62.

Sorensen, A. L., Reis, C. A., Tarp, M. A., Mandel, U., Ramachandran, K., Sankaranarayanan, V., Schwientek, T., Graham, R., Taylor-Papadimitriou, J., Hollingsworth, M. A., Burchell, J. & Clausen, H. (2006). Chemoenzymatically synthesized multimeric Tn/STn MUC1 glycopeptides elicit cancer-specific anti-MUC1 antibody responses and override tolerance. *Glycobiology*, 16, 96-107.

Springer, G. F. (1984) T and Tn, General Carcinoma Auto-Antigens. *Science*, 224, 1198-1206.

Takeuchi, H., Kato, K., da-Nagai, K., Hanisch, F. G., Clausen, H. & Irimura, T. (2002). The epitope recognized by the unique anti-MUC1 monoclonal antibody MY.1E12 involves sialyl alpha 2-3galactosyl beta 1-3N-acetylgalactosaminide linked to a distinct threonine residue in the MUC1 tandem repeat. *J. Immunol. Methods*, 270, 199-209.

Yamamoto, M., Bhavanandan, V. P., Nakamori, S. & Irimura, T. (1996). A novel monoclonal antibody specific for sialylated MUC1 mucin. *Jpn. J. Cancer Res.*, 87, 488-496.

---

What is claimed is:

1. A method of inducing a cancer specific immune response toward MUC1 comprising immunization of a mammal with an immunogenic glycopeptide comprising a GSTA (SEQ ID NO 2) motif, wherein the GSTA motif is present in a tandem repeat, wherein said GSTA motif is 0-glycosylated at least at the T-residue or at the S-residue of the GSTA (SEQ ID NO 2) motif wherein the sequence of the tandem repeat is VTSAPDTRPAPGSTAPPAHG (SEQ ID NO 1), where in the glycosylation pattern of the tandem repeat is selected from the group consisting of:

VT$^{Tn}$SAPDTRPAPGST$^{Tn}$APPAHG

VT$^{Tn}$SAPDTRPAPGS$^{Tn}$T$^{Tn}$APPAHG

VT$^{Tn}$SAPDT$^{Tn}$RPAPGS$^{Tn}$T$^{Tn}$APPAHG

VT$^{Tn}$S$^{Tn}$APDTRPAPGS$^{Tn}$T$^{Tn}$APPAHG

VT$^{Tn}$S$^{Tn}$APDT$^{Tn}$RPAPGS$^{Tn}$T$^{Tn}$APPAHG

VT$^{STn}$SAPDTRPAPGST$^{STn}$APPAHG

VT$^{STn}$SAPDTRPAPGS$^{STn}$T$^{STn}$APPAHG

VT$^{STn}$SAPDT$^{STn}$RPAPGS$^{STn}$T$^{STn}$APPAHG

VT$^{STn}$S$^{STn}$APDTRPAGS$^{STn}$T$^{STn}$APPAHG

VT$^{STn}$S$^{STn}$APDT$^{STn}$RPAPGS$^{STn}$T$^{STn}$APPAHG;

wherein the cancer is selected from the group consisting of breast cancer, ovarian cancer, pancreatic cancer, or lung cancer.

2. The method of claim 1, wherein the immune response toward MUC1 is either innate immunity, humoral immunity, cellular immunity or any combinations thereof.

3. The method according to claim 1, wherein said MUC1 is aberrantly glycosylated and expressed on cancer cells.

4. The method according to claim 1, wherein the immunogenic glycopeptide comprises more than two tandem repeats.

5. The method according to claim 1, wherein the immunogenic glycopeptide comprises more than one tandem repeat.

6. The method according to claim 1, wherein the immunogenic glycopeptide is coupled to a carrier selected from the group consisting of: human serum albumin, keyhole limpet hemocyanin (KLH), thyroglobulin, ovalbumin, influenza hemagglutinin, PADRE polypeptide, malaria circumsporozite (CS) protein, hepatitis B surface antigen (HBSAgI9-2s), Heat Shock Protein (HSP) 65, *Mycobacterium tuberculosis*, cholera toxin, cholera toxin mutants with reduced toxicity, diphtheria toxin, CRM 97 protein that is cross-reactive with diphtheria toxin, recombinant Streptococcal C5a peptidase, *Streptococcus pyogenes* ORF1224, *Streptococcus pyogenes* ORF1664, *Streptococcus pyogenes* ORF2452, *Chlamydia* pneumonia ORF T367, *Chlamydia pneumoniae* ORF T858, Tetanus toxoid and HIVgp120T1.

7. The method according to claim 1, wherein the mammal is selected from the group consisting of: a human, a mouse, a rat, a rabbit, a sheep, a goat, and a dog.

8. A composition comprising an immunogenic glycopeptide comprising a GSTA (SEQ ID NO 2) motif, wherein the GSTA motif is present in a tandem repeat, wherein said GSTA motif is O-glycosylated at least at the T-residue or at the S-residue of the GSTA (SEQ ID NO 2) motif wherein the sequence of the tandem repeat is VTSAPDTRPAPGSTAPPAHG (SEQ ID NO 1), where in the glycosylation pattern of the tandem repeat is selected from the group consisting of:

$VT^{Tn}SAPDTRPAPGST^{Tn}APPAHG$ $VT^{Tn}SAPDTRPAPGS^{Tn}T^{Tn}APPAHG$ $VT^{Tn}SAPDT^{Tn}RPAPGS^{Tn}T^{Tn}APPAHG$ $VT^{Tn}S^{Tn}APDTRPAPGS^{Tn}T^{Tn}APPAHG$ $VT^{Tn}S^{Tn}APDT^{Tn}RPAPGS^{Tn}T^{Tn}APPAHG$ $VT^{STn}SAPDTRPAPGST^{STn}APPAHG$ $VT^{STn}SAPDTRPAPGS^{STn}T^{STn}APPAHG$ $VT^{STn}SAPDT^{STn}RPAPGS^{STn}T^{STn}APPAHG$

-continued $VT^{STn}S^{STn}APDTRPAGS^{STn}T^{STn}APPAHG$ $VT^{STn}S^{STn}APDT^{STn}RPAPGS^{STn}T^{STn}APPAHG$.

9. The composition according to claim 8, said composition being a pharmaceutical composition.

10. The composition according to claim 8, wherein the composition is a cancer vaccine for treatment or prevention of breast cancer, ovarian cancer, pancreatic cancer, or lung cancer.

11. A method of treating or preventing cancer in a mammal comprising administrating a pharmaceutical composition comprising an immunogenic glycopeptide comprising a GSTA (SEQ ID NO 2) motif, wherein the GSTA motif is present in a tandem repeat, wherein said GSTA motif is 0-glycosylated at least at the T-residue or at the S-residue of the GSTA (SEQ ID NO 2) motif wherein the sequence of the tandem repeat is VTSAPDTRPAPGSTAPPAHG (SEQ ID NO 1), where in the glycosylation pattern of the tandem repeat is selected from the group consisting of:

$VT^{Tn}SAPDTRPAPGST^{Tn}APPAHG$ $VT^{Tn}SAPDTRPAPGS^{Tn}T^{Tn}APPAHG$ $VT^{Tn}SAPDT^{Tn}RPAPGS^{Tn}T^{Tn}APPAHG$ $VT^{Tn}S^{Tn}APDTRPAPGS^{Tn}T^{Tn}APPAHG$ $VT^{Tn}S^{Tn}APDT^{Tn}RPAPGS^{Tn}T^{Tn}APPAHG$ $VT^{STn}SAPDTRPAPGST^{STn}APPAHG$ $VT^{STn}SAPDTRPAPGS^{STn}T^{STn}APPAHG$ $VT^{STn}SAPDT^{STn}RPAPGS^{STn}T^{STn}APPAHG$ $VT^{STn}S^{STn}APDTRPAGS^{STn}T^{STn}APPAHG$ $VT^{STn}S^{STn}APDT^{STn}RPAPGS^{STn}T^{STn}APPAHG$;

wherein the cancer is selected from the group consisting of breast cancer, ovarian cancer, pancreatic cancer, or lung cancer.

* * * * *